(12) United States Patent
Watkins et al.

(10) Patent No.: US 6,596,723 B1
(45) Date of Patent: Jul. 22, 2003

(54) FUNGAL EFFLUX PUMP INHIBITORS

(75) Inventors: Will J. Watkins, Sunnyvale, CA (US); Remy Lemoine, San Francisco, CA (US); Aesop Cho, Mountain View, CA (US); Thomas E. Renau, San Carlos, CA (US)

(73) Assignee: Essential Therapeutics, Inc., Mountain View, CA (US)

( * ) Notice: Subject to any disclaimer, the term of this patent is extended or adjusted under 35 U.S.C. 154(b) by 0 days.

(21) Appl. No.: 09/906,864

(22) Filed: Jul. 16, 2001

(51) Int. Cl.7 .................... A61K 31/495; A61K 31/517; C07D 239/72; C07D 209/00; C07D 209/48
(52) U.S. Cl. .................. 514/252.17; 514/259; 544/287; 544/322; 541/1; 548/465; 548/469; 548/473
(58) Field of Search ............................ 514/252.17, 259; 544/287, 322; 546/1; 548/465, 469, 473

(56) References Cited

FOREIGN PATENT DOCUMENTS

WO  2001030757  *  5/2001

OTHER PUBLICATIONS

Debnath et al, CAS Abstr, 131:266552–1999:499893, also cited as J. Med. Chem. 42/17,3203–9(1999).*
Debnath etal, J.Med.Chem., 42/17/3203–3209 (1999), "Structure based ID of small Molecule Antiviral Cpds."*

* cited by examiner

*Primary Examiner*—Mukund J. Shah
*Assistant Examiner*—Sudhaker B. Patel
(74) *Attorney, Agent, or Firm*—Bernard F. Rose; Bingham McCutchen LLP

(57) ABSTRACT

This invention relates to compounds that are efflux pump inhibitors and therefore are useful as potentiators of antifungal agents for the treatment of infections caused by fungi that employ an efflux pump resistance mechanism.

36 Claims, No Drawings

FUNGAL EFFLUX PUMP INHIBITORS

FIELD OF THE INVENTION

The present invention relates to their fields of organic chemistry, biochemistry, medicinal chemistry, microbiology and medicine. In particular, it relates to organic compounds that are fungal efflux pump inhibitors.

BACKGROUND OF THE INVENTION

The information provided and the references cited herein are not admitted, nor should they be construed, to be prior art to the present invention, but are provided solely to assist the understanding of the reader.

Fungal infections are relatively rare in immuno-competent patients. In fact, a number of Candida species are often present as benign commensal organisms in the digestive system of healthy individuals (Shepherd, et al., *Ann. Rev. Microbiol.*, 1985, 39:579–614). Fungal infections, however, can be life threatening for immuno-compromised patients. Three major groups of immuno-compromised individuals have emerged in recent years: (1) cancer patients undergoing chemotherapy, (2) organ transplant patients being treated with immuno-suppressants, and (3) AIDS patients. Data from the National Nosocomial Infections Surveillance System conducted in the United States showed a 487 percent increase in Candida bloodstream infections between 1980 and 1989 (Rinaldi, et al., *Antimicrob. Ag. Chemother.*, 1995, 39:1–8). Oropharyngeal candidiasis was shown to be the most common fungal infection complication associated with AIDS, studies suggesting that up to 90% of AIDS patients have had at least one episode of the infection (Powderly, *AIDS research and Human Retroviruses*, 1994, 10:925–929).

There are relatively few clinically useful anti-fungal agents. Among those available to treat serious fungal infection are amphotericin B, flucytosine, fluconazole, itraconazole and ketoconazole (Odds, *J. Antimicrob. Chemother.*, 1993, 31:463–471). A more recent addition to the arsenal of effective compounds is posaconazole. However, resistance to these drugs is developing rapidly. Take, for example, fluconazole.

Fluconazole is currently the most extensively used anti-fungal agent for the treatment of patients with severe candidiasis. It has higher water solubility and a longer plasma half-life than other azoles and has relatively low toxicity. Between 1988 and 1993, fluconazole was used to treat over 15 million patients, including at least 250,000 AIDS patients (Hitchcock, *Biochem. Soc. Trans.*, 1993, 21:1039–1047). Given this wide-spread use, it comes as no surprise that the appearance of fluconazole-resistant Candida strains has been reported (Rex, et al., *Antimicrob. Ag. Chemother.*, 1995, 39:1–8; Vanden Bossche, et al., 1994, supra). In some cases the resistance was found to be due to mutations in *C. albicans* itself, while in other cases, Candida species less suceptible to fluconazole, such as *C. glabrata* and *C. krusei*, replaced *C. albicans* as the infecting organism (Odds, 1993, supra).

The mechanism of resistance to fluconazole appears to be multifaceted. In one study, amplification of the CYP51 gene (encoding the fluconazole target P-450 protein C14 demethylase) was implicated (Vanden Bossche, et al., *Antimicrob. Agents and Chemother.*, 1994, 36: 2602–2610). In another study, resistance was correlated with the appearance of an altered P-450 target protein with decreased affinity for fluconazole (Hitchcock, *Biochem Soc. Trans.*, 1993, 21:1039–1047). However, fluconazole resistance appears to be primarily related to decreased accumulation of the drug in resistant cells (Vanden Bossche, et al., 1994; Odds, 1993, supra). Species intrinsically resistant to fluconazole, such as *C. glabrata*, *C. krusei* and *Aspergillus fumigatus*, have also been shown to accumulate less fluconazole (Vanden Bossche et al., 1994, supra). *C. glabrata* and *C. krusei*, on the other hand, have been shown to accumulate itraconazole and therefore are susceptible to that compound (Marichal et al., *Mycoses*, 1995, 38:111–117). Thus, it appears that both intrinsic and acquired resistance may be due to decreased drug accumulation in the cell. There are several ways in which a cell can manipulate the concentration of a compound including barring entrance in the first place, decomposition of the compound once it gains access to the interior of the cell or simply excreting the compound before it can have any effect on the cell. This latter approach is called efflux and the cell components that effect efflux, i.e., membrane transporter proteins, are called efflux pumps.

Efflux pumps are ubiquitous in all types of cells, from bacterial to mammalian (Higgins, *Ann. Rev. Cell Biol.*, 1992, 8:67–113). Efflux is driven either by the energy of ATP hydrolysis (ABC-transporter superfamily) or by proton transfer (Major Facilitator superfamily).

Efflux pumps exhibit differing degrees of specificity. Some are extremely specific, such as the TetA efflux pump in gram-negative bacteria, which effluxes tetracycline only. Others are less specific; e.g., the MsrA protein in *Staphyloccus aureus* effluxes not only erythromycin but related macrolides as well. Then there are efflux pumps that are quite general in their effluxing capability, excreting a variety of structurally unrelated compounds from a cell. Many efflux pumps are clinically significant. For example, resistance to chemotherapeutics in some mammalian cancer cells has been attributed to a P-glycoprotein multi-drug resistant efflux pump (Gottesman, et al., *Ann. Rev. Biochem.*, 1993, 62:385–427). *Pseudomonas aeruginosa*, the causal agent of respiratory infections, adventitious infection in burn patients, etc., uses Mex efflux pumps to eliminate quinolones, as well as other structurally unrelated antibiotics (Nikaido, *Science*, 1994, 264:382–388). Multiple-drug resistant (MDR) pumps have been implicated in fluconazole resistance in *C. albicans* and *C. glabrata* (Parkinson, et al., *Antimicrob. Agents Chemother.*, 1995, 39:1696–1699; Sanglard, et al., *Antimicrob. Agents Chemother.*, 1995, 39:2378–2386; Albertson, et al., *Antimicrob. Agents Chemother.*, 1996, 40:2835–2841).

What would be useful would be a compound that inhibits the activity of fungal efflux pumps so that anti-fungal agents can accumulate in fungal cells in sufficient quantity to exert their effect. The present invention provides such compounds.

SUMMARY OF THE INVENTION

The present invention relates to compounds that are fungal efflux pump inhibitors. When administered, in combination with a therapeutic anti-fungal agent, to a patient suffering from a infection caused by a fungus species that employs efflux pump(s), the compounds inhibit the activity of the pump(s) so that the anti-fungal agent can accumulate in sufficient concentration in the fungal cells to treat the infection.

Thus, in one aspect, the present invention relates to a fungal efflux pump inhibitory compound having the chemical structure:

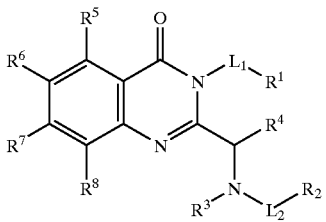

wherein:
L¹ is selected from the group consisting of a single bond and $C_x^1$;
R¹ is selected from the group consisting of:
(C₃–C₇)heteroalicyclic containing 1 nitrogen atom and 0 to 2 additional heteroatoms independently selected from the group consisting of nitrogen, oxygen and sulfur wherein the heteroalicyclic is substituted with one or more substituents independently selected from the group consisting of hydrogen, halo, hydroxy, $-C_x^2$, $=O$, $-OC_x^2$, $-C_x^2OC_x^3$, $-C_x^2OH$, $-C_x^2(halo)$, $-C_x^2OC(=O)C_x^3$, $-C_x^2NHC(=O)C_x^3$, $-C_x^2NHC(=NH)C_x^3$, $-NHC_x^2$, $-NC_x^2C_x^3$, $-C_x^2NH_2$, $-C_x^2NHC_x^3$, $-C_x^2NC_x^3C_x^4$ and $-C=C-C=C-$, wherein the end carbons of the group are covalently bonded to adjacent carbon atoms of the heteroalicyclic ring to form a carbocyclic ring, the adjacent carbon atoms of the heteroalicyclic being double-bonded to one another such that the carbocyclic ring formed is a phenyl group;
$-C_x^2NHC(=NH)C_x^3$; $-C_x^2NC_x^3C(=NH)C_x^{13}$ and, $-C_x^2NHC(=O)C_x^3$;
L² is selected from the group consisting of $-C(O)-$, $-S(O)_2-$, $-C(O)O-$, $-C(O)NH-$, $-C(O)NC_x^5-$, $-C(S)NH-$, $-C(S)NC_x^5-$, $-C(NH)NH-$, $-C(NH)NC_x^5-$, $-S(O)_2NH-$; and $-S(O)_2NC_x^5-$;
R² is selected from the group consisting of:
aryl substituted with one or more groups independently selected from the group consisting of hydrogen, halo, $-C_x^6$, $-C_x^6(halo)$, $-C_x^6OH$, $-C_x^6OC_x^7$ and $-OC_x^8$; and, $C_x^8$;
R³ is selected from the group consisting of aryl substituted with 1 or more substituents independently selected from the group consisting of hydrogen, halogen, hydroxy, $-C_x^9$, $-OC_x^9$, $-NH_2$, $-NHC_x^9$, $-NC_x^9C_x^{10}$, $-CO_2H$, $-CO_2C_x^9$, $-C(O)C_x^9$, $-C(O)NH_2$, $C(O)NHC_x^9$ and $C(O)NC_x^9C_x^{10}$;
R⁴ is selected from the group consisting of $C_x^{11}$;
R⁵, R⁶, R⁷ and R⁸ are independently selected from the group consisting of hydrogen, halo, $-C_x^{12}$, $-OC_x^{12}$ and $-O(C_x^{12})O-$; $C_x^1$, $C_x^2$, $C_x^3$, $C_x^4$, $C_x^5$, $C_x^6$, $C_x^7$, $C_x^8$, $C_x^9$, $C_x^{10}$, $C_x^{11}$, $C_x^{12}$ and $C_x^{13}$ are independently (C₁–C₄)alkyl; and,
the absolute stereochemistry of centers of asymmetry are independently R or S; or, a pharmaceutically acceptable salt thereof.

As aspect of this invention is a compound wherein L¹ is a single bond.

An aspect of this invention is a compound in which R¹ is a heteroalicyclic.

An aspect of this invention is the above compound wherein the heteroalicyclic is selected from the group consisting of

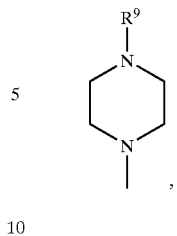

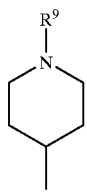

and

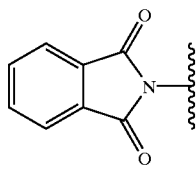

wherein R⁹ is selected from the group consisting of hydrogen, $-C_x^2$, $-C_x^2Cl$, $-C_x^2OH$ and $-C_x^2OC(O)C_x^3$.

An aspect of this invention is the above compound wherein the heteroalicyclic is

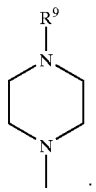

An aspect of this invention is the above compound wherein R⁹ is selected from the group consisting of CH₃—, —CH₂CH₂Cl, —CH₂CH₂OH and —CH₂OC(O)CH₃.

An aspect of this invention is the above compound wherein R⁹ is CH₃—.

An aspect of this invention is a compound wherein R² is phenyl substituted with one or more groups independently selected from the group consisting of hydrogen, halo, $-C_x^4$ and $C_x^4O-$.

An aspect of this invention is a compound wherein R² is phenyl optionally substituted with one or more groups independently selected from the group consisting of fluorine, chlorine, CH₃ — and CH₃O—.

An aspect of this invention is a compound wherein L² is selected from the group consisting of $-C(O)O-$, $-C(O)NH-$, $-C(O)-$ and $-S(O)_2-$.

An aspect of this invention is a compound wherein R³ is phenyl substituted with one or more groups independently selected from the group consisting of hydrogen, $C_x^5-$, $C_x^5O-$ and $-O(C_x^5)O-$.

An aspect of this invention is a compound wherein R³ is phenyl substituted with one or more groups independently selected from the group consisting of hydrogen, CH₃—, CH₃O— and —OCH₂O—.

An aspect of this invention is a compound wherein $R^4$ is $CH_3$—.

An aspect of this invention is a compound wherein $R^5$, $R^6$, $R^7$ and $R^8$ are independently selected from the group consisting of hydrogen, halo, —$C_x^5$ and $C_x^5O$—.

An aspect of this invention is a compound wherein $R^5$, $R^6$, $R^7$ and $R^8$ are independently selected from the group consisting of hydrogen, fluorine and chlorine.

An aspect of this invention is a compound wherein:
L1 is a single bond; and,
R1 is

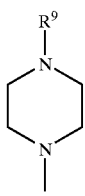

wherein $R_9$ is $CH_3$.

An aspect of this invention is a method for inhibiting the growth or proliferation of a fungal cell that employs an efflux pump resistance mechanism, comprising contacting the fungal cell with a anti-fungal agent and a fungal efflux pump inhibitor having the chemical structure:

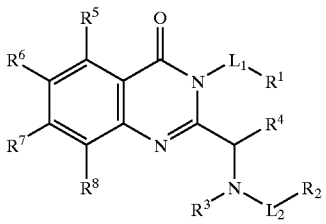

wherein:
  $L^1$ is selected from the group consisting of a single bond and $C_x^1$;
  $R^1$ is selected from the group consisting of:
    ($C_3$–$C_7$)heteroalicyclic containing 1 nitrogen atom and 0 to 2 additional heteroatoms independently selected from the group consisting of nitrogen, oxygen and sulfur wherein the heteroalicyclic is substituted with one or more substituents independently selected from the group consisting of hydrogen, halo, hydroxy, —$C_x^2$, =O, —$OC_x^2$, —$C_x^2OC_x^3$, —$C_x^2OH$, —$C_x^2$(halo), —$C_x^2OC(=O)C_x^3$, —$C_x^2NHC(=O)C_x^3$, —$C_x^2NHC(=NH)C_x^3$, —$NHC_x^2$, —$NC_x^2C_x^3$, —$C_x^2NH_2$, —$C_x^2NHC_x^3$, —$C_x^2NC_x^3C_x^4$ and —C=C—C=C—, wherein the end carbons of the group are covalently bonded to adjacent carbon atoms of the heteroalicyclic ring to form a carbocyclic ring, the adjacent carbon atoms of the heteroalicyclic being double-bonded to one another such that the carbocyclic ring formed is a phenyl group;
    —$C_x^2NHC(=NH)C_x^3$; —$C_x^2NC_x^3C(=NH)C_x^{13}$ and, —$C_x^2NHC(=O)C_x^3$;
  $L^2$ is selected from the group consisting of —C(O)—, —S(O)$_2$—, —C(O)O—, —C(O)NH—, —C(O)NC_x^5—, —C(S)NH—, —C(S)NC_x^5—, —C(NH)NH—, —C(NH)NC_x^5—, —S(O)$_2$NH—; and —S(O)$_2$NC_x^5—;
  $R^2$ is selected from the group consisting of:

aryl substituted with one or more groups independently selected from the group consisting of hydrogen, halo, —$C_x^6$, —$C_x^6$(halo), —$C_x^6OH$, —$C_x^6OC_x^7$ and —$OC_x^8$; and,
  $C_x^8$;
  $R^3$ is selected from the group consisting of aryl substituted with 1 or more substituents independently selected from the group consisting of hydrogen, halogen, hydroxy, —$C_x^9$, —$OC_x^9$, —$NH_2$, —$NHC_x^9$, —$NC_x^9C_x^{10}$, —$CO_2H$, —$CO_2C_x^9$, —$C(O)C_x^9$, —$C(O)NH_2$, $C(O)NHC_x^9$ and $C(O)NC_x^9C_x^{10}$;
  $R^4$ is selected from the group consisting of $C_x^{11}$;
  $R^5$, $R^6$, $R^7$ and $R^8$ are independently selected from the group consisting of hydrogen, halo, —$C_x^{12}$, —$OC_x^{12}$ and —$O(C_x^{12})O$—;
  $C_x^1$, $C_x^2$, $C_x^3$, $C_x^4$, $C_x^5$, $C_x^6$, $C_x^7$, $C_x^8$, $C_x^9$, $C_x^{10}$, $C_x^{11}$, $C_x^{12}$ and $C_x^{13}$ are independently ($C_1$–$C_4$)alkyl; and,
the absolute stereochemistry of centers of asymmetry are independently R or S; or, a pharmaceutically acceptable salt thereof.

In another aspect of this invention the anti-fungal agent is an azole anti-fungal agent.

In another aspect of this invention, the azole anti-fungal agent is selected from the group consisting of fluconazole and posaconazole.

In still another aspect of this invention, a fungal cell is first contacted with an efflux pump inhibitor herein and then contacted with the anti-fungal agent.

In an aspect of this invention, a fungal cell is contacted with the efflux pump inhibitor herein and the anti-fungal agent simultaneously.

In an aspect of this invention, the fungal cell is a genus Candida cell.

In an aspect of this invention, the genus Candida cell is selected from the group consisting of *C. albicans, C. krusei, C. tropicalis, C. parapsilosis* and *C. glabrata*.

In an aspect of this invention, the fungal cell is a genus Aspergillus cell.

In an aspect of this invention the genus Aspergillus cell is an *Aspergillus fumigatus cell*.

An aspect of this invention is a method for treating an infection caused by a fungus that employs an efflux pump resistance mechanism, comprising administering to a patient in need thereof a therapeutically effective amount of an anti-fungal agent and an efflux pump inhibitor having the chemical structure:

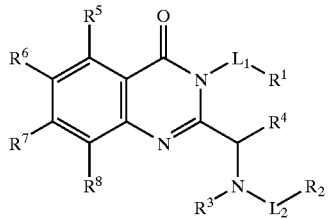

wherein:
  $L^1$ is selected from the group consisting of a single bond and $C_x^1$;
  $R^1$ is selected from the group consisting of:
    ($C_3$–$C_7$)heteroalicyclic containing 1 nitrogen atom and 0 to 2 additional heteroatoms independently selected from the group consisting of nitrogen, oxygen and sulfur wherein the heteroalicyclic is substituted with one or more substituents independently selected from the group consisting of hydrogen, halo, hydroxy, $-C_x^2$, =O, $-OC_x^2$, $-C_x^2OC_x^3$, $-C_x^2OH$, $-C_x^2(halo)$, $-C_x^2OC(=O)C_x^3$, $-C_x^2NHC(=O)C_x^3$, $-C_x^2NHC(=NH)C_x^3$, $-NHC_x^2$, $-NC_x^2C_x^3$, $-C_x^2NH_2$, $-C_x^2NHC_x^3$, $-C_x^2NC_x^3C_x^4$ and $-C=C-C=C-$, wherein the end carbons of the group are covalently bonded to adjacent carbon atoms of the heteroalicyclic ring to form a carbocyclic ring, the adjacent carbon atoms of the heteroalicyclic being double-bonded to one another such that the carbocyclic ring formed is a phenyl group; $C_x^2NHC(=NH)C_x^3$; $-C_x^2NC_x^3C(=NH)C_x^3$ and, $-C_x^2NHC(=O)C_x^3$;

$L^2$ is selected from the group consisting of $-C(O)-$, $-S(O)_2-$, $-C(O)-$, $-C(O)NH-$, $-C(O)NC_x^5-$, $-C(S)NH-$, $-C(S)NC_x^5-$, $-C(NH)NH-$, $-C(NH)NC_x^5-$, $-S(O)_2NH-$; and $-S(O)_2NC_x^5-$;

$R^2$ is selected from the group consisting of:
aryl substituted with one or more groups independently selected from the group consisting of hydrogen, halo, $-C_x^6$, $-C_x^6(halo)$, $-C_x^6OH$, $-C_x^6OC_x^7$ and $-OC_x^8$; and,
$C_x^8$;

$R^3$ is selected from the group consisting of aryl substituted with 1 or more substituents independently selected from the group consisting of hydrogen, halogen, hydroxy, $-C_x^9$, $-OC_x^9$, $-NH_2$, $-NHC_x^9$, $-NC_x^9C_x^{10}$, $-CO_2H$, $-CO_2C_x^9$, $-C(O)C_x^9$, $-C(O)NH_2$, $C(O)NHC_x^9$ and $C(O)NC_x^9C_x^{10}$;

$R^4$ is selected from the group consisting of $C_x^{11}$;

$R^5$, $R^6$, $R^7$ and $R^8$ are independently selected from the group consisting of hydrogen, halo, $-C_x^{12}$, $-OC_x^{12}$ and $-O(C_x^{12})O-$;

$C_x^1$, $C_x^2$, $C_x^3$, $C_x^4$, $C_x^5$, $C_x^6$, $C_x^7$, $C_x^8$, $C_x^9$, $C_x^{10}$, $C_x^{11}$, $C_x^{12}$ and $C_x^{13}$ are independently $(C_1-C_4)$alkyl; and, the absolute stereochemistry of centers of asymmetry are independently R or S; or, a pharmaceutically acceptable salt thereof.

It is an aspect of this invention that the infection is caused by a genus Candida fungus.

It is an aspect of this invention that the genus Candida fungus is *C. albicans, C. krusei, C. tropicalis, C. parapsilosis* or *C. glabrata*.

It is an aspect of this invention that the infection is caused by a genus Aspergillus fungus.

It is an aspect of this invention that the genus Aspergillus fungus is *Aspergillus fumigatus*.

It is an aspect of this invention that, when treating an infection, the efflux pump inhibitor and the anti-fungal agent are administered to the organism simultaneously.

It is an aspect of this invention that, when treating an infection, the efflux pump inhibitor is administered to the organism followed by administration of the anti-fungal agent.

An aspect of this invention is a pharmaceutical composition comprising a pharmaceutically acceptable carrier or excipient; and, an efflux pump inhibitor having the chemical structure:

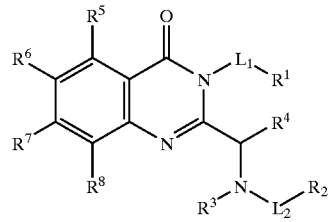

wherein:
$L^1$ is selected from the group consisting of a single bond and $C_x^1$;

$R^1$ is selected from the group consisting of:
$(C_3-C_7)$heteroalicyclic containing 1 nitrogen atom and 0 to 2 additional heteroatoms independently selected from the group consisting of nitrogen, oxygen and sulfur wherein the heteroalicyclic is substituted with one or more substituents independently selected from the group consisting of hydrogen, halo, hydroxy, $-C_x^2$, =O, $-OC_x^2$, $-C_x^2OC_x^3$, $-C_x^2OH$, $-C_x^2(halo)$, $-C_x^2OC(=O)C_x^3$, $-C_x^2NHC(=O)C_x^3$, $-C_x^2NHC(=NH)C_x^3$, $-NHC_x^2$, $-NC_x^2C_x^3$, $-C_x^2NH_2$, $-C_x^2NHC_x^3$, $-C_x^2NC_x^3C_x^4$ and $-C=C-C=C-$, wherein the end carbons of the group are covalently bonded to adjacent carbon atoms of the heteroalicyclic ring to form a carbocyclic ring, the adjacent carbon atoms of the heteroalicyclic being double-bonded to one another such that the carbocyclic ring formed is a phenyl group;
$-C_x^2NHC(=NH)C_x^3$, $-C_x^2NC_x^3C(=NH)C_x^{13}$ and, $-C_x^2NHC(=O)C_x^3$;

$L^2$ is selected from the group consisting of $-C(O)-$, $-S(O)_2-$, $-C(O)O-$, $-C(O)NH-$, $-C(O)NC_x^5-$, $-C(S)NH-$, $-C(S)NC_x^5-$, $-C(NH)NH-$, $-C(NH)NC_x^5-$, $-S(O)_2NH-$; and $-S(O)_2NC_x^5-$;

$R^2$ is selected from the group consisting of:
aryl substituted with one or more groups independently selected from the group consisting of hydrogen, halo, $-C_x^6$, $-C_x^6(halo)$, $-C_x^6OH$, $-C_x^6OC_x^7$ and $-OC_x^8$; and,
$C_x^8$;

$R^3$ is selected from the group consisting of aryl substituted with 1 or more substituents independently selected from the group consisting of hydrogen, halogen, hydroxy, $-C_x^9$, $-OC_x^9$, $-NH_2$, $-NHC_x^9$, $-NC_x^9C_x^{10}$, $-CO_2H$, $-CO_2C_x^9$, $-C(O)C_x^9$, $-C(O)NH_2$, $C(O)NHC_x^9$ and $C(O)NC_x^9C_x^{10}$;

$R^4$ is selected from the group consisting of $C_x^{11}$;

$R^5$, $R^6$, $R^7$ and $R^8$ are independently selected from the group consisting of hydrogen, halo, $-C_x^{12}$, $-OC_x^{12}$ and $-O(C_x^{12})O-$;

$C_x^1$, $C_x^2$, $C_x^3$, $C_x^4$, $C_x^5$, $C_x^6$, $C_x^7$, $C_x^8$, $C_x^9$, $C_x^{10}$, $C_x^{11}$, $C_x^{12}$, and $C_x^{13}$ are independently $(C_1-C_4)$alkyl; and, the absolute stereochemistry of centers of asymmetry are independently R or S; or, a pharmaceutically acceptable salt thereof.

An aspect of this invention is the above composition further comprising a therapeutically effective amount of an anti-fungal agent.

It is an aspect of this invention that the anti-fungal agent is an azole anti-fungal agent.

It is an aspect of this invention that the azole anti-fungal agent is fluconazole or posaconazole.

DETAILED DESCRIPTION OF THE INVENTION

Brief Description of the Tables

Table 1 provides the IUPAC names of the representative compounds of this invention described in the Synthesis section hereof.

Table 2 provides data regarding the potentiation, by representative compounds of this invention, of fluconazole against a *Candida albicans* strain over-expressing CDR1 and CDR2 efflux pumps.

Table 3 provides data regarding the potentiation, by representative compounds of this invention, of fluconazole against a *Candida glabrata* strain over-expressing $C_gCDR1$ and $C_gCDR2$ efflux pumps.

Table 4 provides data regarding the potentiation, by representative compounds of this invention, of fluconazole against clinical isolates of *C. tropicalis, C. krusei* and *C. parapsilosis*.

Table 5 provides data regarding the potentiation, by representative compounds of this invention, of posaconazole against *Aspergillis fumigatus*.

Definitions

As used herein, the term "alkyl" refers to a straight or branched chain saturated aliphatic hydrocarbon. Preferably, the alkyl group consists of 1 to 20 carbon atoms (whenever a numerical range such as "1–20" or "1 to 20" is provided herein, it means that the group may consist of 1 carbon atom, 2 carbon atoms, 3 carbon atoms, etc., up to and including 20 carbon atoms). More preferably, an alkyl group of this invention is a medium size alkyl having 1 to 10 carbon atoms. Most preferably, it is a lower alkyl having 1 to 4 carbon atoms. The size of an alkyl may be indicated by the formula $(C_a-C_b)$alkyl where a and b are integers from 1 to 20 and indicate how may carbons are in the alkyl chain. For example, a $(C_1-C_4)$alkyl refers to a straight or branched chain alkyl consisting of 1, 2, 3 or 4 carbon atoms. An alkyl group may be substituted or unsubstituted. When substituted, the substituent group(s) is preferably one or more independently selected from the group consisting of halo, hydroxy, alkoxy, acyloxy, amino, acylamino, amido, carboxy, carbonyl, alkylcarbonyl, alkoxycarbonyl, cyano and nitro.

A "cycloalkyl" group refers to a 3 to 8 member all-carbon monocyclic ring. The designation $(C_3-C_6)$cycloalkyl, for example, refers to a 3-, 4-, 5- or 6-member all-carbon ring. A cycloaklyl group may contain one or more double bonds but it does not contain a fully conjugated pi-electron system; i.e., it is not aromatic. Examples, without limitation, of cycloalkyl groups are cyclopropane, cyclobutane, cyclopentane, cyclopentene, cyclohexane, cyclohexadiene, adamantane, cycloheptane and, cycloheptatriene. A cycloalkyl group may be substituted or unsubstituted. When substituted, the substituent group(s) is preferably one or more independently selected from the group consisting of halo, hydroxy, alkoxy, acyloxy, amino, acylamino, amido, carboxy, carbonyl, alkylcarbonyl, alkoxycarbonyl, cyano and nitro.

An "alkenyl" group refers to an alkyl group, as defined herein, having at least two carbon atoms and at least one carbon-carbon double bond. As used herein, $(C_2-C_4)$ alkenyl, for example, refers to a 2, 3, or 4 carbon alkenyl group.

An "aryl" group refers to an all-carbon monocyclic or a fused-ring polycyclic (i.e., rings which share adjacent pairs of carbon atoms) group having a completely conjugated pi-electron system. Examples, without limitation, of aryl groups are phenyl, naphthalenyl and anthracenyl. The aryl group may be substituted or unsubstituted. When substituted, the substituted group(s) is preferably one or more independently selected from the group consisting of alkyl, halo, $(halo)_3C—$, hydroxy, alkoxy, acyloxy, amino, acylamino, amido, carboxy, carbonyl, alkylcarbonyl, alkoxycarbonyl, cyano and nitro.

As used herein, a "heteroaryl" group refers to a monocyclic or fused ring in which one or more of the rings contains one or more atoms selected from the group consisting of nitrogen, oxygen and sulfur and, in addition, sufficient double bonds to establish a fully conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. A heteroaryl group may be substituted or unsubstituted. When substituted, the substituted group(s) is preferably one or more independently selected from the group consisting of alkyl, halo, $(halo)_3C—$, hydroxy, alkoxy, acyloxy, amino, acylamino, amido, carboxy, carbonyl, alkylcarbonyl, alkoxycarbonyl, cyano and nitro.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted. When substituted, the substituted group(s) is preferably one or more independently selected from the group consisting of alkyl, halo, $(halo)_3C—$, hydroxy, alkoxy, acyloxy, amino, acylamino, amido, carboxy, carbonyl, alkylcarbonyl, alkoxycarbonyl, cyano and nitro.

A "halo" group refers to fluorine, chlorine, bromine or iodine.

A "hydroxy" group refers to an —OH group.

An "alkoxy" group refers to an —O(alkyl) group.

An "acyloxy" group refers to an —OC(O)(alkyl) group.

An "amino" group refers to an —NRR' group wherein R and R' are independently selected from the group consisting of hydrogen and alkyl, wherein the alkyl group is not further substituted.

An "acylamino" group refers to a —NRC(O)(alkyl) group wherein R is selected from the group consisting of hydrogen and unsubstituted alkyl.

An "amido" group refers to a —C(O)NRR' group wherein R and R' are independently selected from the groups consisting of hydrogen and alkyl, the alkyl group being not further substituted.

A "carboxy" group refers to a —C(O)OH group.

A "carbonyl" group refers to a —C(O)H group.

An "alkylcarbonyl" group refers to a —C(O)(alkyl) group.

An "alkoxycarbonyl" group refers to a —C(O)O(alkyl) group wherein the alkyl group is not further substituted.

A "cyano" group refers to a —C≡N group.

A "nitro" group refers to a —$NO_2$ group.

The term "efflux pump" refers to a protein assembly which exports molecules from the cytoplasm or periplasm of a cell to the external environment in an energy dependent fashion.

An "efflux pump inhibitor" is a compound which interferes with the ability of an efflux pump to export molecules from a cell. In particular, the efflux pump inhibitors of this invention interfere with a pump's ability to excrete therapeutic anti-fungal agents from fungal cells.

By a fungus that "employs an efflux pump resistance mechanism" is meant that the fungal cells are known or are shown to excrete anti-fungal agents from their cytoplasm or periplasm to the external environment and thereby reduce the concentration of the anti-fungal agent in the cells to below that necessary to inhibit the growth and/or proliferation of the cells.

In the context of cell growth, the term "inhibit" means that the rate of growth and/or proliferation of a cellular population is decreased, preferably stopped. By "stopped" is preferably meant permanently; that is, the cells are killed. Inhibition can be monitored by, for example, comparing the difference in turbidity of liquid cultures, or the difference in plaque size for cultures on solid media, in the presence and absence of an inhibitory agent.

As used herein, the term "overproduces" refers to the presence in a fungal strain of a significantly larger number of an efflux pump or pumps than that found in most naturally-occurring (i.e., usually non-nosocomial) isolates of that strain. The term does not refer merely to the presence of a larger number of the component polypeptides of an efflux pump, but rather to the presence of a larger number of functional efflux pumps in the membranes of the cell. A strain that overproduces an efflux pump would, of course, be expected to more efficiently export substrate molecules.

A "wild-type" strain, on the other hand, produces an efflux pump or pumps at the level that is typical of natural isolates of a particular fungal species. In general, a wild-type strain will produce an efflux pump or pumps at a significantly lower level than a related strain which is stated to "overproduce" a pump or pumps.

As used herein, the term "anti-fungal agent" refers to a compound that is either fungicidal or fungistatic. A fungicide kills fungal cells while a fungistat slows or stops cell growth and/or proliferation so long as the compound is present. The efflux pump inhibitors of this invention may be somewhat fungicidal or fungistatic in their own right, but their primary utility resides in their ability to potentiate other anti-fungal agents by inhibiting efflux pump activity in resistant fungal strains.

An "azole" anti-fungal agent refers to any member of those classes of anti-fungal agents characterized by the inclusion of one or more imidazole or triazole rings in their chemical structure. Examples, without limitation of anti-fungal azole compounds are butoconazole, clotrimazole, fenticonazole, ketoconazole, sulfconazole, fluconazole, itraconazole, terconazole, posaconazole, triticonazole, imibenconazole and metaconazole.

By "potentiation" of an anti-fungal agent is meant that a compound of this invention counteracts the resistance mechanism in a particular fungal strain such that an anti-fungal agent can inhibit the growth and/or proliferation of fungal cells at a lower concentration than in the absence of the compound.

A "sub-inhibitory concentration" of an anti-fungal agent refers to a concentration that is less than that required to inhibit a majority of the cells in a population of a fungal species. Generally, a sub-inhibitory concentration refers to a concentration that is less than the Minimum Inhibitory Concentration (MIC), which is defined, unless specifically stated to be otherwise, as the concentration required to produce an 80% reduction in the growth or proliferation of a target fungus.

As used herein, the term "treat," treatment," or "treating" refers to the administration of a therapeutically or prophylactically effective amount of a composition comprising a compound of this invention and an antifungal agent to a patient in need of such treatment.

As used herein, "infect," or "infection" refers to the establishment in a patient of a population of a fungus that results in a deleterious effect on the health or well-being of the patient and/or gives rise to discernable symptoms associated with the particular fungus.

A "pharmaceutical composition" refers to a mixture of one or more of the compounds described herein, or physiologically acceptable salts or prodrugs thereof, with other chemical components, such as pharmaceutically acceptable carriers and excipients. The purpose of a pharmaceutical composition is to facilitate administration of a compound to a patient.

A "pharmaceutically acceptable salt" of a compound of this invention refers to the compound in a charged form together with a counter-ion. In general, the compound of this invention will be a positively charged species usually in the form of an ammonium cation. In such case, the negatively charged counter-ion may be, for example, without limitation, chloride, bromide, iodide, nitrate, phosphate, sulfate, acetate, propionate, butyrate, maleate, fumarate, methanesulfonate, ethanesulfonate, 2-hydroxyethylsulfonate, n-propylsulfonate isopropylsulfonate, lactate, malate or citrate. Pharmaceutically acceptable salts in which the compound of this invention forms the positively-charged species are obtained by reacting the compound with an appropriate acid.

A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

A further example of a prodrug might be a short polypeptide, for example, without limitation, a 2–10 amino acid polypeptide, bonded through a terminal amino group to a carboxy group of a compound of this invention or through a terminal carboxy group with an amino group of a compound herein, wherein the polypeptide is hydrolyzed or metabolized in vivo to release the active molecule.

As used herein, a "pharmaceutically acceptable carrier" refers to a carrier or diluent that does not cause significant irritation to a patient and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the terms "prevent", "preventing" and "prevention" refer to a method for barring a patient from acquiring a fungal infection in the first place.

As used herein, the terms "treat", "treating" and "treatment" refer to a method of alleviating or abrogating a fungal infection and/or its attendant symptoms once a patient has been infected.

As used herein, "administer," administering," or "administration" refers to the delivery to a patient of a compound, salt or prodrug of the present invention or of a pharmaceutical composition containing a compound, salt or prodrug of this invention to a patient for the purpose of inhibiting a fungal efflux pump. It also refers to the delivery of a composition comprising a compound, salt or prodrug of this invention in combination with an anti-fungal agent, in which case the purpose is the treatment or prevention of a fungal infection.

The term "patient" refers to any living entity capable of being infected by a fungus. In particular, a "patient" refers to a mammal such as a dog, cat, horse, cow, pig, rabbit, goat or sheep. Most particularly, a patient refers to a human being.

The term "therapeutically effective amount" as used herein refers to that amount of a compound of this invention together with an anti-fungal agent, which will relieve to some extent one or more of the symptoms of the disorder being treated. In reference to the treatment of a fungal infection, a therapeutically effective amount refers to that amount of a compound of this invention and an anti-fungal agent, which has the effect of (1) reducing, preferably eliminating, the population of fungal cells in the patient's body, (2) inhibiting (i.e., slowing, preferably stopping) proliferation of the fungal cells, (3) inhibiting to some extent (i.e., slowing, preferably stopping) spread of the infection, and/or, (4) relieving to some-extent (preferably, eliminating) one or more symptoms associated with a particular fungal infection.

The term "prophylactically effective amount" refers to that amount of a compound of this invention and an anti-fungal agent that, when administered subsequent to a therapeutically effective amount has the effect of (1) maintaining a reduced level of the population of fungal cells achieved by the therapeutically effective amount; (2) maintaining the level of inhibition of proliferation of the fungal cells achieved by the therapeutically effective amount; (3) maintaining the degree of inhibition of spread of the infection achieved by the therapeutically effective amount; and/or (4) maintaining the level of relief of one or more symptoms or, or if symptoms were eliminated, maintaining the non-existence of symptoms associated with a fungal infection achieved by the therapeutically effective amount of the compound of this invention. A prophylactically effective amount also refers to that amount of a composition comprising a compound of this invention and an anti-fungal agent that will prohibit a fungus from accumulating in a susceptible organism in sufficient amount to cause an infection. An example of a susceptible organism would be an immuno-compromised patient such as one that has undergone transplant surgery and therefore is being treated with immuno-suppressants, or a person suffering from AIDS.

"In vitro" refers to procedures performed in an artificial environment such as, e.g., without limitation, in a test tube or culture medium.

"In vivo" refers to procedures performed within a living organism such as, without limitation, a mouse, rat or rabbit.

Discussion

The present invention relates to the inhibition of efflux pump activity in fungal species and, thereby, the potentiation of anti-fungal agents. The identification and use of efflux pump inhibitors is generally discussed in Chambedand et al., Internat. Patent Appl. No. PCT/US96/05469, WO96/33285, entitled "Efflux Pump Inhibitors." The following is a description of several efflux pumps that confer resistance to fluconazole on Candida albicans. The description is exemplary only and is not intended to limit the scope of this invention in any way whatsoever.

Three MDR pumps have been demonstrated to confer resistance to fluconazole in clinical isolates of *C. albicans* (Sanglard et al., 1996, *Antimicrob. Ag. Chemother.* 40:2300–2305). These pumps are CDR1 (ABC-family, Prasad et al., 1995, *Curr. Genet.,* 27:320–329), CDR2 (ABC-family, Sanglard et al, 1996, supra) and BenR (MF-family, Benyaakov et al., 1994). The genes which encode the former, e.g., cdr1 and cdr2, have been shown to be over-expressed in several *C. albicans* isolates from AIDS patients with whom fluconazole therapy has failed. It has also been shown that the strains that over-express these genes were cross-resistant to ketoconazole and itraconazole. Over-expression of benR, on the other hand, conferred resistance to fluconazole only. To further define the resistance mechanism, *C. albicans* strains were prepared in which the genes expressing individual pumps were deleted. Strains were also produced having multiple gene deletions to further study specificity of the pumps and their role in intrinsic resistance to azole anti-fungals. CDR1 was shown to play a significant role in the intrinsic resistance of *C. albicans* to azoles, as deletion of the cdr1 gene rendered the strain more susceptible. CDR2 and BenR were shown to also contribute to intrinsic resistance, but deletion of the corresponding genes enhanced intrinsic resistance only when cdr1 was also deleted. A *C. albicans* mutant which was deprived of all known efflux pumps was at least 30-fold more susceptible to azole anti-fungal agents than the parent strain.

In another study, two homologs of cdr1 and benR, cgcdr and cgben, were cloned from resistant *C. glabrata* suggesting that a similar resistance mechanism was at work in this species also. Furthermore, an active efflux pump in azole-resistant *Aspergillus nidulans* has also been identified (Waard and van Nistelrooy, 1980, *Pesticide Biochem. Physiol.* 13:255–266).

From the above studies, it appears that, in general, strains that are cross-resistant to several anti-fungal azoles tend to over-express CDR1-type broad-spectrum pumps while strains that are resistant only to fluconazole over-express the narrow-spectrum BenR-type pump.

Compounds of this invention are capable of effectively inhibiting many of the above efflux pumps. They may be used to combat both intrinsic and acquired resistance and thus may in fact expand the spectrum of activity of anti-fungal agents against previously non-susceptible species.

The compounds of this invention are particularly effect in overcoming efflux pump-mediated resistance to azole anti-fungals, expecially fluconazole and posaconazole.

Synthesis

The following are exemplary procedures for synthesizing representative compounds of this invention. Neither the syntheses nor the compounds prepared are to be construed as limiting the scope of this invention in any manner whatsoever. Other approaches to the synthesis of the compounds will become apparent to those skilled in the art based on the disclosures herein and are within the scope of this invention.

Compound 1

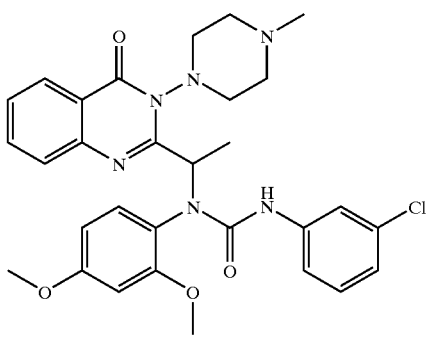

Step 1:

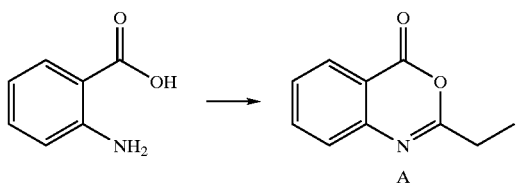

A solution of anthranilic acid (15 g, 109.4 mmol) in 21 mL (164.1 mmol) of propionic anhydride was stirred at 100° C. for 1.5 hours. The excess propionic anhydride was evaporated (15 torr, 80° C. water bath). The crude mass was co-evaporated three times with toluene to give A (18.723 g, 98%).

$^1$H-NMR (300 MHz, DMSO-$d_6$) δ: 1.23 (t, J=7.8 Hz, 3H), 2.67 (q, J=7.8 Hz, 2H), 7.50–7.65 (m, 2H), 7.89 (dt, J=7.6, 1.8 Hz, 1H), 8.07 (dd, J=7.6, 1.8 Hz, 1H).

Step 2:

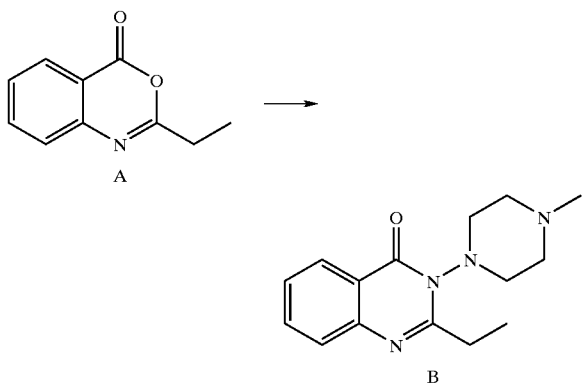

To a suspension of A (18.723 g, 107.0 mmol) in 28 mL of acetic acid was dropwise added 1-amino-4-methylpiperazine (13.48 mL, 112.0 mmol). The mixture was stirred at 90° C. for 14 hours before being evaporated and co-evaporated three times with toluene. The residue was dissolved in water and the pH of the solution was adjusted to 3 by addition of 1M aqueous hydrochloric acid. The aqueous layer was extracted three times with ethyl ether and the combined organic layers were discarded. The aqueous layer was basified to pH 11 by addition of 2M aqueous sodium hydroxide. After saturation by addition of solid sodium chloride and three extractions with ethyl acetate, the combined organic layers were washed with water, dried over sodium sulfate, filtered through cotton and evaporated in vacuo to give B (20.714 g, 71%).

$^1$H-NMR (300 MHz, DMSO-$d_6$) δ: 1.23 (t, J=7.3 Hz, 3H), 2.15 (m, 2H), 2.21 (s, 3H), 2.76 (m, 2H), 2.80–2.95 (m, 4H), 3.96 (m, 2H), 7.45 (dt, J=8.1, 1.5 Hz, 7.58 (dd, J=8.1, 1.5 Hz, 1H), 7.76 (dt, J=8.1, 1.5 Hz, 1H), 8.06 (dd, J=8.1, 1.5 Hz, 1H).

Step 3:

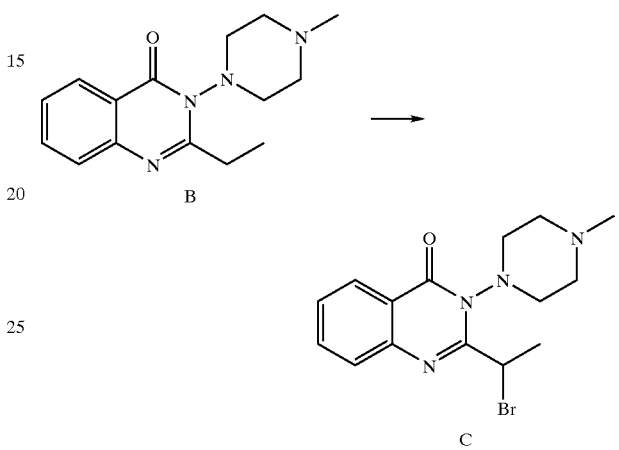

To a solution of B (5 g, 18.4 mmol) and sodium acetate (3.4 g, 41 mmol) in 30 mL of acetic acid was added pyridinium tribromide (11.8 g, 37 mmol). The resulting mixture was stirred at 50° C. for two hours before being cooled to 0° C. The precipitate that formed was filtered off and washed with acetic acid and hexanes. The resulting powder was suspended in water and the pH was adjusted to 9 by addition at 0° C. of a saturated solution of aqueous potassium carbonate. The white solid that remained was filtered, rinsed with water and dried in vacuo to give C (4.2 g, 65%).

$^1$H-NMR (300 MHz, DMSO-$d_6$) δ: 2.01 (d, J=6.6 Hz, 3H), 2.28 (s, 3H), 2.34 (m, 2H), 2.85 (m, 2H), 3.04 (m, 2H), 3.94–4.03 (m, 2H), 5.72 (q, J=6.6 Hz, 1H), 7.55 (dt, J=8.1, 1.5 Hz, 1H), 7.68 (dd, J=8.1 Hz, 1.5 Hz, 1H), 7.84 (dt, J=8.1, 1.5 Hz, 1H), 8.12 (dd, J=8.1, 1.5 Hz, 1H).

MS (ES+) m/z 351/353 (M$^+$+H).

Step 4:

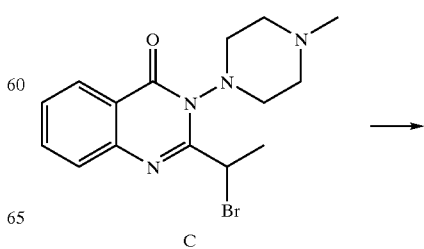

-continued

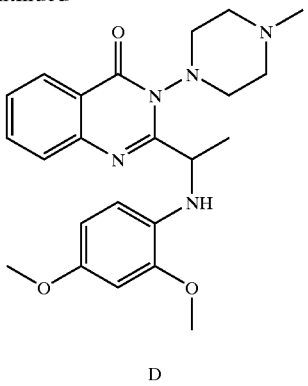

D

A suspension of C (1.5 g, 4.27 mmol), 2,4-dimethoxyaniline.(0.785 g, 5.12 mmol), and potassium carbonate (0.708 g, 5.12 mmol) in 11 mL of anhydrous dimethylformamide was stirred at 85° C. for 4.5 hours. The resulting mixture was diluted with water and extracted three times with a 3/1 (v/v) mixture of ethyl acetate and hexanes. The combined organic layers were washed with water, dried over sodium sulfate, filtered, and evaporated to give a dark brown oil which was purified by flash chromatography on silica gel (ethyl acetate/methanol 100/0 to 97.5/2.5 to 95/5 to 90/10) to give D (1.688 g, 69%).

$^1$H-NMR (300 MHz, CDCl$_3$) δ: 1.59 (d, J=6.6 Hz, 3H), 2.26–2.50 (m, 2H), 2.39 (s, 3H), 2.78–3.00 (m, 4H), 3.71 (s, 3H), 3.86 (s, 3H), 4.27, 4.34 (2m, 2H), 5.20 (q, J=6.6 Hz, 1H), 6.34 (dd, J=8.7, 2.5 Hz, 1H), 6.44 (d, J=2.5 Hz, 1H), 6.61 (d, J=8.7 Hz, 1H), 7.40 (dt, J=8.1, 1.5 Hz, 1H), 7.58–7.74 (m, 2H), 8.20 (dd, J=8.1, 1.5 Hz, 1H).

MS (ES+) m/z 424 (M$^+$+H).

Step 5:

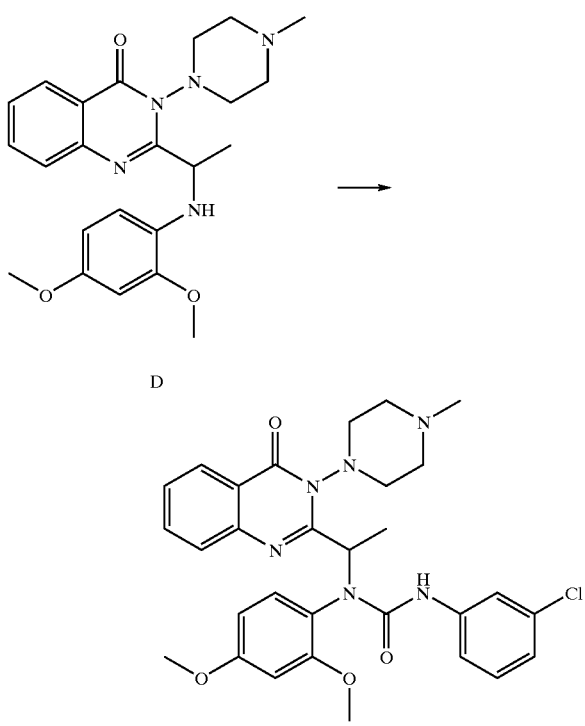

At 0° C., 3-chlorophenyl isocyanate (165 mL, 1.36 mmol) in 1.5 mL of 1,2-dichloromethane was dropwise added to a solution of D (0.522 g, 1.23 mmol) in 6.5 mL of 1,2-dichloroethane. The resulting mixture was stirred at 0° C. to room temperature for 5 hours before being evaporated in vacuo. The residue was purified by flash chromatography on silica gel to give 0.574 g of Compound 1 in neutral form (81% yield) as a white solid.

$^1$H-NMR (300 MHz, DMSO-d$_6$), mixture of atropisomers, δ: 1.06 (d, J=6.9 Hz, 3H), 2.06–2.30 (m, 2H), 2.17 (s, 3H), 2.66–2.8 (m, 1H), 2.8–3.0 (m, 1H) 3.22–3.32 (m, 2H), 3.7–3.8 (m, 6H), 4.06 (m, 2H), 6.00 (q, J=6.9 Hz, 1H), 6.54 (dd, J=8.7, 1.1 Hz, 1H), 6.69 (d, J=1.9 Hz, 1H), 6.90 (d, J=7.8 Hz, 1H), 7.13 (t, J=8.1 Hz, 1H), 7.31 (d, J=8.1 Hz, 1H), 7.40–7.86 (m, 5H), 8.11 (d, J=8.1 Hz, 1H).

MS (ES+) m/z 577 (M$^+$+H).

The neutral form of Compound 1 (0.574 g, 0.995 mmol) was suspended in 4.49 mL of a 0.21 M aqueous solution of methanesulfonic acid. The resulting suspension was stirred at room temperature for one hour before being filtered through a Rainin nylon filter (0.3 U/13 mm). The filtrate was lyophilized to give 0.368 mg of Compound 1 as the mesylate salt.

$^1$H-NMR (300 MHz, D$_2$O), mixture of atropisomers, δ (water peak at 4.64 ppm, non-corrected): 1.18, 1.36 (2d, J=7.2 Hz, 3H), 2.67, 2.74, 2.80 (3s+1m, 8H), 3.00–3.80 (m, 12H), 6.10–6.24 (m, 2H), 6.54–6.68 (m, 2H), 6.90–7.22 (m, 4H), 7.31 (d, J=8.7 Hz, 1H), 7.44–7.54 (m, 1H), 7.66–7.78 (m, 1H), 8.08 (d, J=8.1 Hz, 1H).

Compound 2

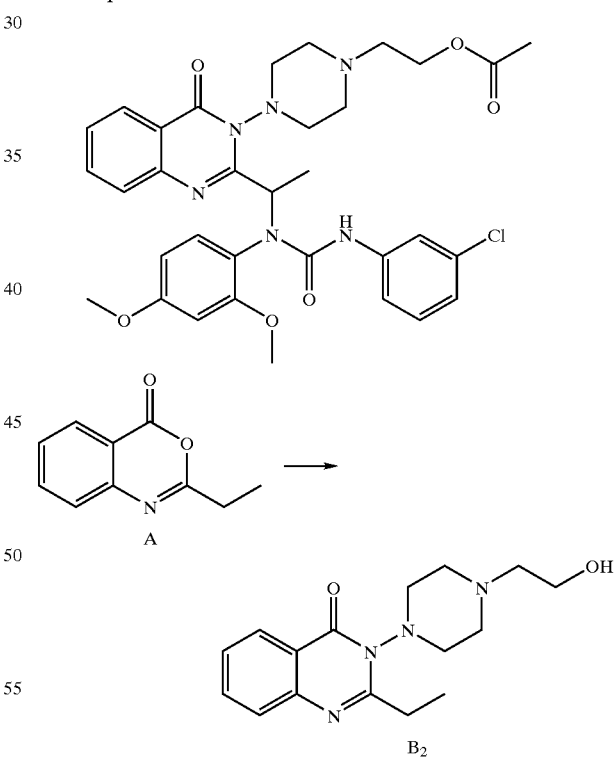

A solution of A (1.2 g, 6.21 mmol) and 1-amino-4-(2-hydroxyethyl)piperazine (1 g, 6.89 mmol) in 10 mL of a 1/1 (v/v) mixture of anhydrous pyridine and absolute ethanol was stirred at reflux for 14 hours. The resulting mixture was evaporated and co-evaporated three times with toluene. The residue was partitioned between ethyl acetate and 1M aqueous hydrochloric acid. The aqueous layer was extracted with ethyl acetate and the combined organic layers were discarded. The pH of the aqueous layer was adjusted to pH 11 by addition of solid sodium hydroxide and the solution was saturated by addition of solid sodium chloride before being extracted with ethyl acetate. The combined organic layers were washed with water, dried over sodium sulfate, filtered through cotton and evaporated to give $B_2$ (0.816 g, 43%).

$^1$H-NMR (300 MHz, DMSO-$d_6$) δ: 1.34 (s, 3H), 2.23 (dt, J=11.7, 3 Hz, 2H), 2.42 (t, J=6.3 Hz, 2H), 2.75–3.00 (m, 5H), 3.29 (d, J=6.9 Hz, 1H), 3.51 (dt, J=6.9, 6.3 Hz, 2H), 3.96 (dt, J=11.7, 3 Hz, 2H), 4.42 (t, J=6 Hz, 1H), 7.45 (dt, J=7.8, 1.2 Hz, 1H), 7.58 (dd, J=7.8, 1.2 Hz, 1H), 7.76 (dt, J=7.8, 1.2 Hz, 1H), 8.07 (dd, J=7.8, 1.2 Hz, 1H).

Compound 2 was synthesized from $B_2$ using the procedures of Steps 3, 4 and 5, above, with the exception that, during Step 3, the primary hydroxyl group was acetylated.

$^1$H-NMR (300 MHz, CDCl$_3$), mixture of atropisomers, δ: 1.15 (bd, J=6.6 Hz, 3H), 2.03,2.07 (2s, 3H), 2.41–3.10 (m, 7H), 3.47 (bd, J=9.3 Hz, 1H), 3.85 (s, 3H), 3.88 (s, 3H), 4.22 (m, 3H), 4.40 (bt, J=10.5 Hz, 1H), 6.0–6.30 (m, 2H), 6.50–6.70 (m, 2H), 6.88 (bs, 1H), 7.00–7.20 (m, 2H), 7.39 (dt, J=8.1, 1.5 Hz, 1H), 7.50–7.75 (m, 2H), 8.21 (m, 2H).

MS (ES+) m/z 649 (M$^+$+H).

Compound 3

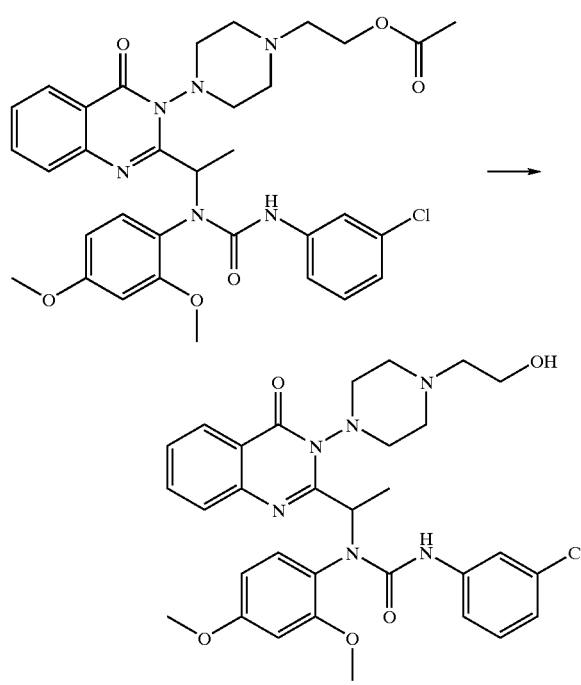

A solution of Compound 2 (0.1 g, 0.154 mmol) in a mixture of methanol, triethylamine and water (8/1/1 by volume, 10 mL) was stirred at room temperature for 14 hours. The resulting mixture was evaporated in vacuo and co-evaporated three times with toluene. The residue was triturated with ethyl acetate and dried to give Compound 3 (0.0403 g, 70%).

$^1$H-NMR (300 MHz, DMSO-$d_6$), mixture of atropisomers, δ: 1.06 (d, J=6.9 Hz, 3H), 2.30 (m, 2H), 2.39 (t, J=6.3 Hz, 2H), 2.87 (bd, J=10.8 Hz, 2H), 3.20–3.30 (m, 1H), 3.40–3.56 (m, 2H), 3.79 (s, 6H), 3.94–4.16 (m, 2H), 4.42 (m, 1H), 6.00 (q, J=6.9 Hz, 1H), 6.56 (m, 1H), 6.69 (d, J=1.8 Hz, 1H), 6.90 (bd, J=7.5 Hz, 1H), 7.14 (t, J=8.1 Hz, 1H), 7.31 (bd, J=8.4 Hz, 1H), 7.44–7.74 (m, 4H), 7.79 (t, J=7.5 Hz, 1H), 8.11 (d, J=7.8 Hz, 1H).

MS (ES+) m/z 607 (M$^+$+H).

Compound 4

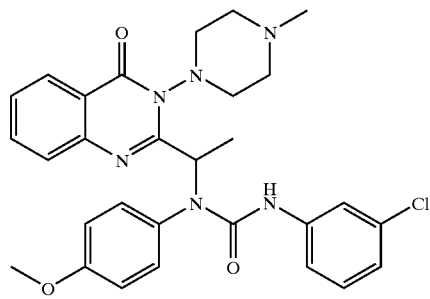

This compound was prepared by procedures analogous to those used for Compound 1.

$^1$H-NMR (300 MHz, CDCl$_3$), mixture of atropisomers, δ: 1.06 (d, J=7.2 Hz, 3H), 2.30–2.50 (m, 4H), 2.8–3.0 (m, 4H), 3.48 (m, 1H), 3.90 (s, 3H), 4.23 (m, 1H), 4.45 (m, 1H), 6.16 (br s, 1H), 6.21 (q, J=7.2 Hz, 1H), 6.9–7.1 (m, 5H), 7.41 (m, 1H), 7.60–7.9 (m, 4H including NH), 8.23 (bd, J=7 Hz, 1H).

MS (ES+) m/z 547/9 (M$^+$+H).

Compound 5

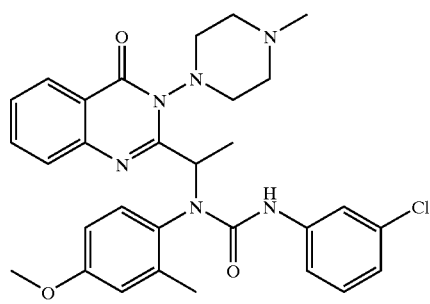

This compound was prepared by procedures analogous to those used for Compound 1.

$^1$H-NMR (as mesylate salt; 300 MHz, CDCl$_3$), mixture of atropisomers, δ: 1.12 and 1.23 (2d, J=7.2 Hz, 3H), 2.1–2.4 (m, 10H), 2.95 (s, 3H, C$\underline{H}_3$SO$_3$), 3.1–3.5 (m, 4H), 3.65–4.0 (m, 4H), 4.5–4.9 (m, 2H), 6.0–6.24 (m, 2H), 6.8–7.15 (m, 5H), 7.2–7.35 (m, 1H+C$\underline{H}$Cl$_3$), 7.45 (m, 1H), 7.65–7.85 (m, 2H), 8.2–8.4 (m, 1H).

Compound 6

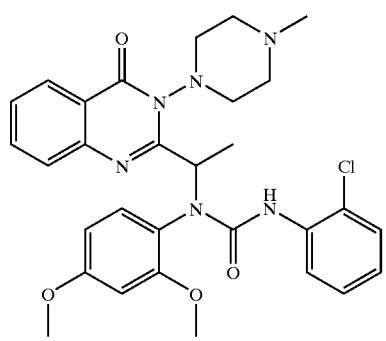

This compound was prepared by procedures analogous to those used for Compound 1.

$^1$H-NMR (300 MHz, CDCl$_3$), mixture of atropisomers, δ: 1.19 (d, J=7.2 Hz, 3H), 2.30–2.50 (m, 4H), 2.7–3.0 (m, 4H), 3.48 (m,1H), 3.86 (s, 3H), 3.89 (s, 3H), 4.21 (m, 1H), 4.42 (m, 1H), 6.15 (q, J=7.2 Hz, 1H), 6.61 (m, 2H), 6.8–6.95 (m, 2H), 7.1–7.2 (m, 2H), 7.40 (m, 1H), 7.67 (m, 2H), 8.1–8.3 (m, 2H).

MS (ES+) m/z 577/9 (M$^+$+H).

Compound 7

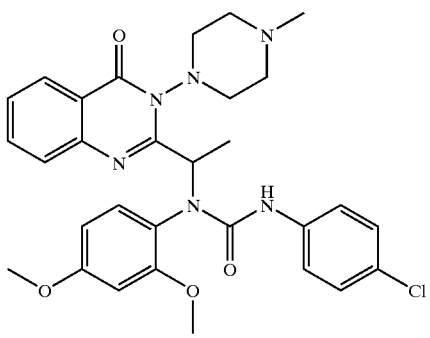

This compound was prepared by procedures analogous to those used for Compound 1.

$^1$H-NMR (300 MHz, CDCl$_3$), mixture of atropisomers, δ: 1.17 (m, 3H), 2.37–2.55 (m, 4H), 2.8–2.95 (m, 4H), 3.45 (m, 1H), 3.88 (s, 6H), 4.21 (m, 1H), 4.42 (m, 1H), 6.17 (br s, 2H), 6.60 (m, 2H), 7.14 (br s, 4H), 7.39 (m, 1H), 7.65 (m, 1H), 8.23 (d, J=8 Hz, 1H).

MS (ES+) m/z 577/9 (M$^+$+H).

Compound 8

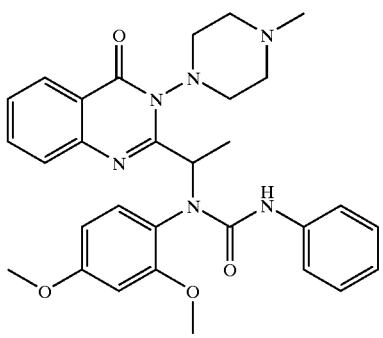

This compound was prepared by procedures analogous to those used for Compound 1.

$^1$H-NMR (300 MHz, CDCl$_3$), mixture of atropisomers, δ: 1.2 (m, 3H), 2.37–2.55 (m, 4H), 2.8–2.95 (m, 4H), 3.45 (m, 1H) 3.88 (br s, 6H), 4.21 (m, 1H), 4.41 (m, 1H), 6.19 (m, 2H), 6.60 (m, 2H), 6.94 (m, 1H), 7.20 (m, 4H), 7.38 (m, 1H), 7.65 (m, 2H), 8.23 (d, J=8 Hz, 1H).

MS (ES+) m/z 543 (M$^+$+H).

Compound 9

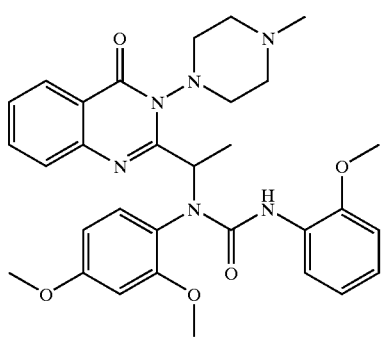

This compound was prepared by procedures analogous to those used for Compound 1.

$^1$H-NMR (300 MHz, CDCl$_3$), mixture of atropisomers, δ: 1.2 (m, 3H), 2.3–2.6 (m, 4H), 2.8–3.0 (m, 4H), 3.4–3.6 (m, 4H), 3.83 (s, 3H), 3.88 (s, 3H), 4.22 (m, 1H), 4.42 (m, 1H), 6.19 (m, 1H), 6.60 (m, 2H), 6.71 (m, 1H), 6.8–7.0 (m, 4H), 7.38 (m, 1H), 7.65 (m, 2H), 8.23 (d, J=8 Hz, 1H).

MS (ES+) m/z 573 (M$^+$+H).

Compound 10

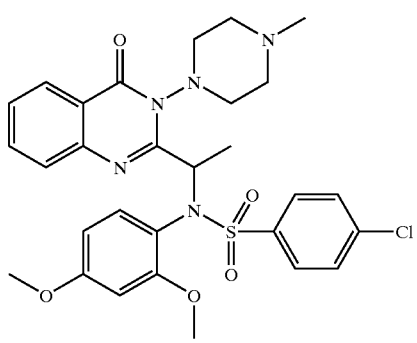

To D (80 mg, 0.19 mmol) dissolved in 3 mL of (CH$_2$)$_2$Cl$_2$ was added 40 μL of triethylamine (0.28 mmol) and 60 mg (0.28 mmol) of 4-chlorobenzenesulfonyl chloride. The clear orange solution was stirred at room temperature for 16 hr then concentrated to dryness. The residue was dissolved in EtOAc and extracted with H$_2$O and washed 2 times with saturated NaHCO$_3$. The organic layer was collected, dried over Na$_2$SO$_4$, filtered and concentrated to dryness. Trituration with hexanes afforded the title compound (113 mg, 100% yield).

$^1$H-NMR (300 MHz, CDCl$_3$), mixture of atropisomers, δ: 1.20 & 1.45 (2d, J=7 Hz, 3H), 2.40–2.6 (m, 4H), 2.8–3.01 (m, 4H), 3.43 (m,1H), 3.7–3.9 (m, 7H), 4.28 (m, 1H), 4.39 (m, 1H), 6.2, 6.47, 6.5 (3m, 3H), 7.08 (m, 2H), 7.31 (m, 2H), 7.43 (m, 1H), 7.67 (m, 1H), 8.04 (d, J=9 Hz, 1H), 8.23 (m, 1H).

MS (ES+) m/z 598 (M$^+$+H).

Compound 11

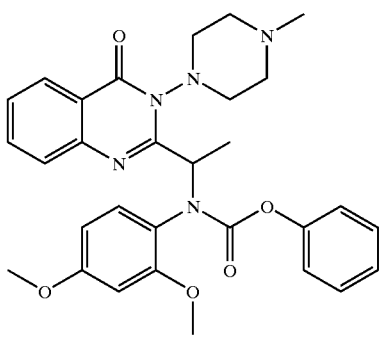

To Intermediate D (82 mg, 0.19 mmol), dissolved in 2.5 mL of $(CH_2)_2Cl_2$, was added 40 µL of triethylamine (0.29 mmol) and 46 mg (0.29 mmol) of phenyl chloroformate. The cloudy pink mixture was stirred at room temperature for 16 hr then concentrated to dryness. The residue was dissolved in EtOAc and extracted with $H_2O$ and washed 2 times with saturated $NaHCO_3$. The organic layer was collected, dried over $Na_2SO_4$, filtered and concentrated to dryness. Trituration with hexanes afforded the title compound (63 mg, 60% yield).

$^1$H-NMR (300 MHz, $CDCl_3$), mixture of atropisomers, δ: 1.24 & 1.58 (2m, 3H), 2.37–2.44 (m, 4H), 2.8–3.01 (m, 4H), 3.35 (m, 1H), 3.7–3.94 (m, 7H), 4.15 (m, 1H), 4.42 (m, 1H), 5.9, 6.5, 6.55 (3m, 3H), 6.95 (m, 2H), 7.10 (m, 2H), 7.23 (m, 1H, with $CHCl_3$), 7.43 (m, 1H), 7.74 (m, 1H), 8.11 (d, J=9 Hz, 1H), 8.25 (m, 1H).

MS (ES+) m/z 544 (M$^+$+H).

Compound 12

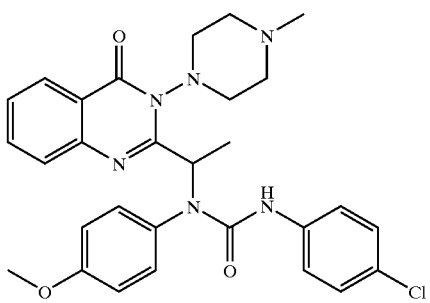

This compound was prepared by procedures analogous to those used for Compound 1.

$^1$H-NMR (300 MHz, $CDCl_3$), mixture of atropisomers, δ: 1.24 (m, 3H), 2.35–2.52 (m, 4H), 2.84–2.96 (m, 4H), 3.45–3.5 (m, 1H), 3.90 (s, 3H), 4.23 (m, 1H), 4.45 (m, 1H), 6.13 (m, 1H), 6.20 (q, J=7 Hz, 1H), 7.02 (m, 2H), 7.14 (s, 5H), 7.41 (m, 1H), 7.66 (m, 2H), 8.23 (d, J=8 Hz, 1H).

MS (ES+) m/z 547/9 (M$^+$+H).

Compound 13

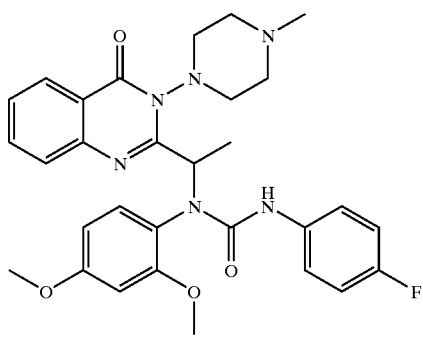

This compound was prepared by procedures analogous to those used for Compound 1.

$^1$H-NMR (300 MHz, $CDCl_3$), mixture of atropisomers, δ: 1.17 (m, 3H), 2.3–2.6 (m, 4H), 2.8–3.0 (m, 4H), 3.4–3.55 (m, 1H), 3.88 (br s, 6H), 4.23 (m, 1H), 4.45 (m, 1H), 6.13 (m, 2H), 6.60 (m, 2H), 6.88 (m, 2H), 7.17 (m, 2H), 7.41 (m, 1H), 7.64 (m, 2H), 8.23 (d, J=8 Hz, 1H).

MS (ES+) m/z 561 (M$^+$+H); 583 (M$^+$+Na).

Compound 14

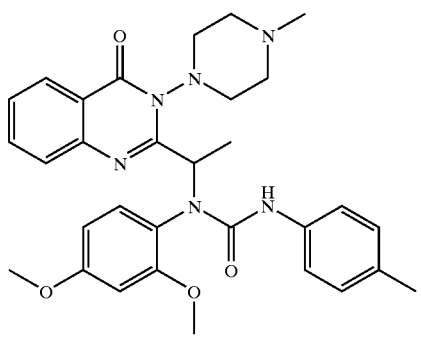

This compound was prepared by procedures analogous to those used for Compound 1.

$^1$H-NMR (300 MHz, $CDCl_3$), mixture of atropisomers, δ: 1.17 (m, 3H), 2.23 (s, 3H), 2.3–2.6 (m, 4H), 2.8–3.0 (m, 4H), 3.4–3.55 (m, 1H), 3.88 (br s, 6H), 4.23 (m, 1H), 4.45 (m, 1H), 6.1–6.2 (m, 2H), 6.60 (m, 2H), 7.0 (m, 2H), 7.07 (m, 2H), 7.39 (m, 1H), 7.63 (m, 2H), 8.23 (d, 1H).

MS (ES+) m/z 557 (M$^+$+H); 579 (M$^+$+Na).

Compound 15

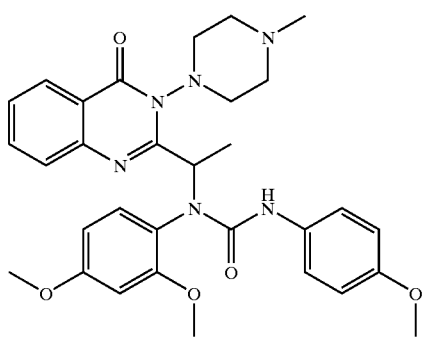

This compound was prepared by procedures analogous to those used for Compound 1.

¹H-NMR (300 MHz, CDCl₃), mixture of atropisomers, δ: 1.2 (m, 3H), 2.3–2.6 (m,4H), 2.8–3.0 (m, 4H), 3.4–3.55 (m, 1H), 3.72 (s, 3H), 3.87 (br s, 6H), 4.2 (m, 1H), 4.42 (m, 1H), 6.03 (m, 1H), 6.18 (m, 1H), 6.58 (m, 2H), 6.74 (bd, J=8 Hz, 2H), 7.1 (m, 2H), 7.38 (m, 1H), 7.66 (m, 2H), 8.23 (d, J=8 Hz, 1H).

MS (ES+) m/z 573 (M⁺+H).

Compound 16

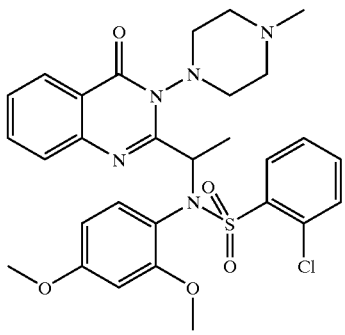

This compound was prepared by procedures analogous to those used for Compound 10.

¹H-NMR (300 MHz, CDCl₃), mixture of atropisomers, δ: 1.27 (d, J=7 Hz, 3H), 2.3–2.6 (m, 4H), 2.8–3.05 (m, 4H), 3.24 (s, 3H), 3.4–3.5 (m, 1H), 3.82 (s, 3H), 4.22 (m, 1H), 4.45 (m, 1H), 6.19 (d, J=2 Hz, 1H), 6.59 (m, 2H), 7.13 (m, 1H), 7.34 (m, 1H), 7.45 (m, 2H), 7.7 (m, 3H), 8.23 (d, J=8 Hz, 1H), 8.57 (d, J=9 Hz, 1H).

MS (ES+) m/z 598/600 (M⁺+H).

Compound 17

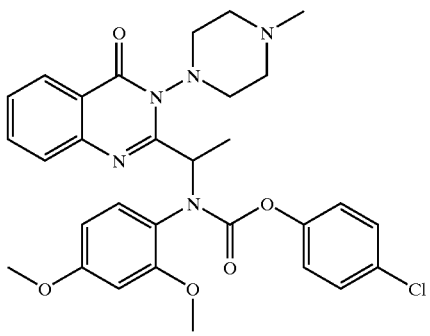

This compound was prepared by procedures analogous to those used for Compound 11.

¹H-NMR (300 MHz, CDCl₃), mixture of atropisomers, δ: 1.21 (d, J=7 Hz, 3H), 2.3–2.6 (m, 4H), 2.8–2.95 (m, 4H), 3.32 (m, 1H), 3.85 (s, 3H), 3.93 (s, 3H), 4.18 (m, 1H), 4.43 (m, 1H), 6.00 (d, J=2 Hz, 1H), 6.54 (m, 2H), 6.90 (d, J=9 Hz, 2H), 7.20 (d, J=9 Hz, 2H), 7.43 (m, 1H), 7.72 (m, 2H), 8.09 (d, J=8 Hz, 1H), 8.24 (d, J=8 Hz, 1H).

MS (ES+) m/z 578/580.

Compound 18

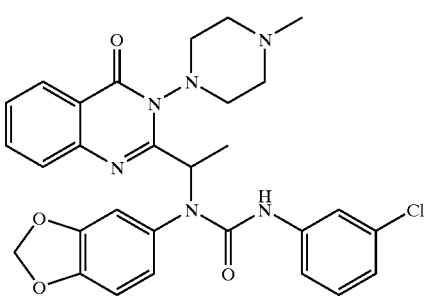

This compound was prepared by procedures analogous to those used for Compound 1.

¹H-NMR (300 MHz, CDCl₃), mixture of atropisomers, δ: 1.21, 1.66 & 2.09 (m, 3H), 2.3–2.6 (m, 4H), 2.8–3.0 (m, 4H), 3.18 & 3.48 (m, 1H), 4.23 (m, 1H), 4.43 (m, 1H), 6.1–6.3 (m, 4H), 6.90 (m, 1H), 7.08 (m, 2H), 7.18 (m, 1H), 7.27 (m, 1H), 7.35–7.5 (m, 2H), 7.6–7.75 (m, 2H), 8.22 (d, J=8 Hz, 1H).

MS (ES+) m/z 561/563.

Compound 19

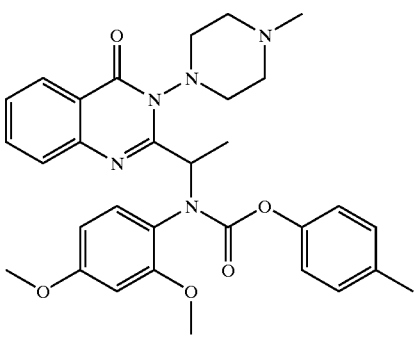

This compound was prepared by procedures analogous to those used for Compound 11.

¹H-NMR (300 MHz, CDCl₃), mixture of atropisomers, δ: 1.21 (d, J=7 Hz, 3H), 2.25 (s, 3H), 2.3–2.6 (m, 4H), 2.8–3.0 (m, 4H), 3.35–3.4 (m, 1H), 3.84 (s, 3H), 3.94 (s, 3H), 4.18 (m, 1H), 4.43 (m, 1H), 6.01 (q, J=7 Hz, 1H), 6.52 (m, 2H), 6.83 (d, J=8 Hz, 2H), 7.04 (d, J=8 Hz, 2H), 7.43 (m, 1H), 7.73 (m, 2H), 8.06 (d, J=9 Hz, 1H), 8.24 (d, J=8 Hz, 1H).

MS (ES+) m/z 558 (M⁺+H).

Compound 20

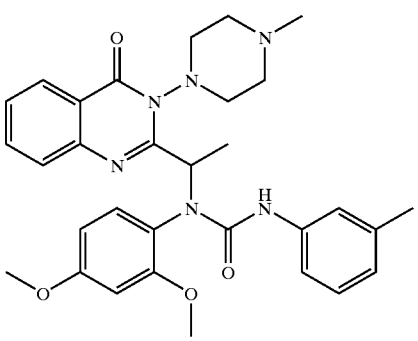

This compound was prepared by procedures analogous to those used for Compound 1.

¹H-NMR (300 MHz, CDCl₃), mixture of atropisomers, δ: 1.17 (m, 3H), 2.24 (s, 3H), 2.3–2.6 (m, 4H), 2.8–3.0 (m, 4H), 3.48 (m, 1H), 3.87 (m, 6H), 4.20 (m, 1H), 4.42 (m, 1H), 6.18 (m, 2H), 6.59 (m, 2H), 6.76 (m, 1H), 7.03 (m, 2H), 7.39 (m, 1H), 7.65 (br s, 2H), 8.22 (m, 2H).

MS (ES+) m/z 557 (M⁺+H).

Compound 21

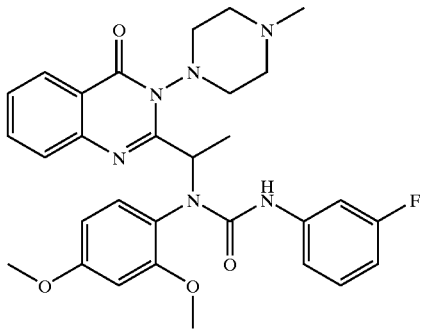

This compound was prepared by procedures analogous to those used for Compound 1.

¹H-NMR (300 MHz, CDCl₃), mixture of atropisomers, δ: 1.17 (m, 3H), 2.3–2.6 (m, 4H), 2.8–3.0 (m, 4H), 3.50 (m, 1H), 3.88 (m, 6H), 4.22 (m, 1H), 4.44 (m, 1H), 6.20 (m, 2H), 6.60 (m, 2H), 6.82 (m, 1H), 7.1 (m, 2H), 7.40 (m, 1H), 7.65 (br s, 2H), 8.22 (m, 2H).

MS (ES+) m/z 561 (M⁺+H).

Compound 22

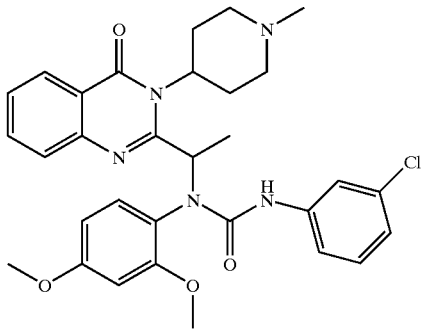

This compound was prepared by procedures analogous to those used for Compound 1.

¹H-NMR (300 MHz, DMSO-d₆), mixture of atropisomers, δ: 1.21, 1.38 (2m, 3H), 3.75 (m, 6H), other aliphatic resonances obscured by solvent and water, 6.2–6.3 (m, 1H), 6.66 (m, 2H), 6.98 (m, 1H), 7.11 (m, 1H), 7.35 (m, 1H), 7.52 (m, 2H), 7.98 (m, 1H), 8.14 (m, 1H).

MS (ES+) m/z 576/578 (M⁺+H).

Compound 23

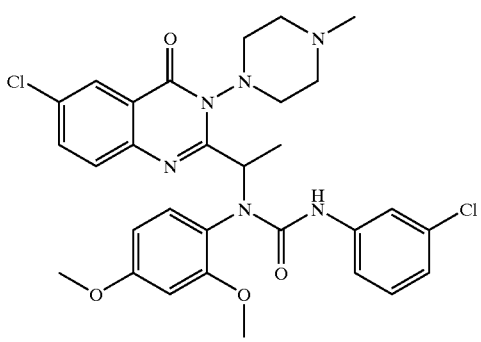

This compound was prepared by procedures analogous to those used for Compound 1, starting from 2-amino-5-chlorobenzoic acid.

¹H-NMR (300 MHz, CDCl₃), mixture of atropisomers, δ: 1.16 (m, 3H), 2.4–2.6 (m, 4H), 2.8–3.0 (m, 4H), 3.50 (m, 1H), 3.88 (m, 6H), 4.22 (m, 1H), 4.42 (m, 1H), 6.18 (m, 2H), 6.60 (m, 2H), 6.91 (m, 1H), 7.08 (m, 2H), 7.59 (m, 2H), 8.09 (m, 1H), 8.20 (s, 1H).

MS (ES+) m/z 611/613/615.

Compound 24

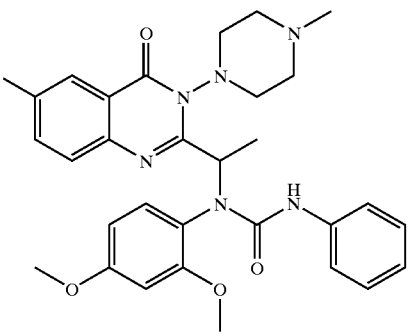

This compound was prepared by procedures analogous to those used for Compound 1, starting from 2-amino-5-chlorobenzoic acid.

¹H-NMR (300 MHz, CDCl₃), mixture of atropisomers, δ: 1.15 (m, 3H), 2.35–2.5 (m, 4H), 2.8–3.0 (m, 4H), 3.50 (m, 1H), 3.88 (m, 6H), 4.20 (m, 1H), 4.41 (m, 1H), 6.15 (m, 2H), 6.60 (m, 2H), 6.94 (m, 1H), 7.18 (m, 3H), 7.59 (m, 2H), 8.12 (m, 1H), 8.19 (s, 1H).

MS (ES+) m/z 577/579.

Compound 25

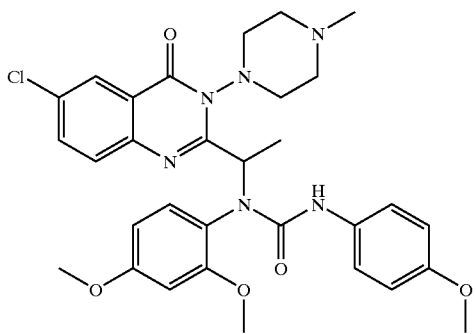

This compound was prepared by procedures analogous to those used for Compound 1, starting from 2-amino-5-chlorobenzoic acid.

¹H-NMR (300 MHz, CDCl₃), mixture of atropisomers, δ: 1.16 (m, 3H), 2.35–2.5 (m, 4H), 2.8–3.1 (m, 4H), 3.49 (m, 1H), 3.72 (s, 3H), 3.87 (m, 6H), 4.19 (m, 1H), 6.00 (m, 1H), 6.14 (m, 1H), 6.58 (m, 1H), 6.74 (m, 2H), 7.08 (m, 2H), 7.59 (m, 2H), 8.10 (m, 1H), 8.19 (s, 1H).

MS (ES+) m/z 607/609 (M⁺+H).

Compound 26

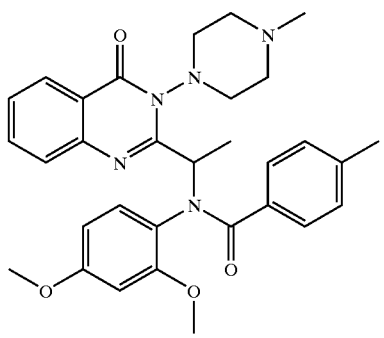

To D (70 mg, 0.17 mmol), dissolved in 2 mL of (CH₂)₂Cl₂, was added 25 μL of triethylamine (0.18.mmol) and 28 mg (0.18 mmol) of p-toluoyl chloride. The cloudy orange mixture was stirred at room temperature for 72 hr at which time a saturated solution of NaHCO₃ was added to the mixture. The organic layer was collected, dried over Na₂SO₄, filtered and concentrated to dryness. Purification of the residue by filtration through SiO₂ (2% to 10% MeOH/CH₂Cl₂) afforded the title compound (85 mg, 96%).

¹H-NMR (300 MHz, CDCl₃), mixture of atropisomers, δ: 1.21 & 1.44 (2d, J=7 Hz, 3H), 2.21 (m, 3H), 2.41–2.54 (m, 4H), 2.8–3.01 (m, 4H), 3.53 (m, 1H), 3.6–3.76 (m, 7H), 4.27 (m, 1H), 4.5 (m, 1H), 6.0, 6.26, 6.42, 6.63 (4m, 3H), 6.91 (m, 2H), 7.18 (m, 2H), 7.45 (m, 1H), 7.74 (m, 1H), 7.85 (d, J=9 Hz, 1H), 8.25 (m, 1H).

MS (ES+) m/z 542 (M⁺+H).

Compound 27

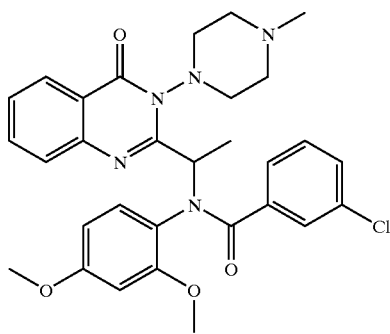

This compound was prepared by procedures analogous to those used for Compound 26.

¹H-NMR (300 MHz, CDCl₃), mixture of atropisomers, δ: 1.22 & 1.47 (2d, J=7 Hz, 3H), 2.4–2.65 (m, 4H), 2.8–3.1 (m, 4H), 3.48 & 3.54 (2m, 1H), 3.71 (s, 3H), 3.77 (s, 3H), 4.29 (m, 1H), 4.49 (m, 1H), 6.01 & 6.27 (m, 1H), 6.35 (q, J=7 Hz, 1H), 6.41 & 6.67 (2m, 1H), 7.0–7.2 (m, 2H), 7.3 (m, 1H, with CHCl₃), 7.43 (m, 1H), 7.7 (m, 2H), 7.95 (d, J=9 Hz, 1H), 8.27 (m, 1H).

MS (ES+) m/z 562/564.

Compound 28

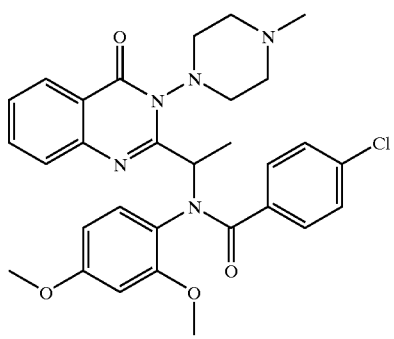

This compound was prepared by procedures analogous to those used for Compound 26.

¹H-NMR (300 MHz, CDCl₃), mixture of atropisomers, δ: 1.21 & 1.45 (2d, J=7 Hz, 3H), 2.4–2.65 (m, 4H), 2.8–3.1 (m, 4H), 3.5 (m, 1H), 3.66 (s, 3H), 3.74 & 3.78 (2s, 3H), 4.30 (m, 1H), 4.50 (m, 1H), 6.02 & 6.26 (m, 1H), 6.4 & 6.62 (m, 2H), 6.41 & 6.67 (2m, 1H), 7.1 (m, 2H), 7.21 (m, 1H with CHCl₃), 7.43 (m, 1H), 7.68 (m, 2H), 7.90 (d, J=9 Hz, 1H), 8.27 (m, 1H).

MS (ES+) m/z 562/564.

Compound 29

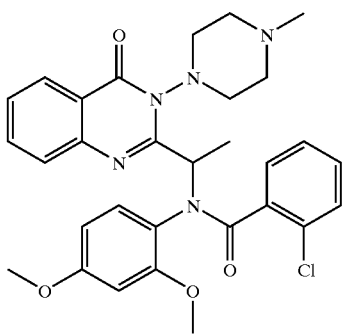

This compound was prepared by procedures analogous to those used for Compound 26.

$^1$H-NMR (300 MHz, CDCl$_3$), mixture of atropisomers, δ: 1.21 & 1.56 (2d, J=7 Hz, 3H), 2.45–2.65 (m, 4H), 2.92 (s, 3H), 3.02 (m, 1H), 3.5–3.9 (m, 7H), 4.29 (m, 1H), 4.55 (m, 1H), 5.85, 6.26 & 6.38 (m, 3H), 6.9–7.25 (m, 4H, with CHCl$_3$), 7.43 (m, 1H), 7.70 (m, 2H), 8.27 (m, 2H).

MS (ES+) m/z 562/564.

Compound 30

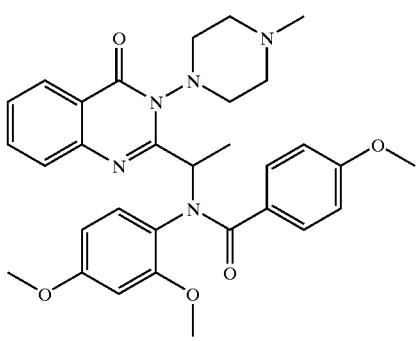

This compound was prepared by procedures analogous to those used for Compound 26.

$^1$H-NMR (300 MHz, CDCl$_3$), mixture of atropisomers, δ: 1.23 & 1.43 (2d, J=7 Hz, 3H), 2.35–2.6 (m, 4H), 2.8–3.05 (m, 4H), 3.52 (m, 1H), 3.6–3.8 (6s, 9H), 4.29 (m, 1H), 4.46 (m, 1H), 6.04, 6.24, 6.63 & 6.87 (4m, 3H), 7.23 (m, 1H, with CHCl$_3$), 7.43 (m, 1H), 7.67 (m, 2H), 7.82 (d, J=9 Hz, 1H), 8.27 (m, 1H).

MS (ES+) m/z 558 (M$^+$+H).

Compound 31

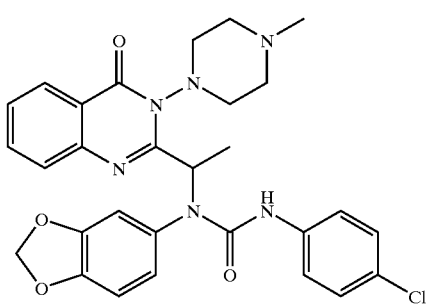

This compound was prepared by procedures analogous to those used for Compound 1.

$^1$H-NMR (300 MHz, CDCl$_3$), mixture of atropisomers, δ: 1.22 & 1.65 (2d, 3H), 2.4–2.6 (m, 4H), 2.85–3.1 (m, 4H), 3.20 & 3.54 (m, 1H), 4.32 (m, 1H), 4.57 (m, 1H), 6.05–6.3 (m, 3H), 6.92 (d, 1H), 7.1–7.35 (m, 3H, with CHCl$_3$), 7.42 (m, 1H), 7.65 (m, 2H), 8.22 (d, 1H).

MS (ES+) m/z 561/563.

Compound 32

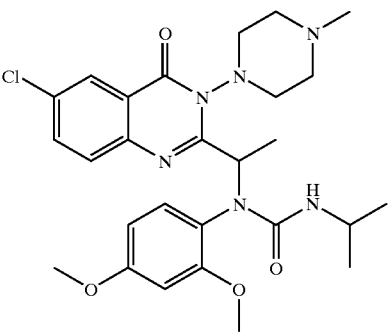

This compound was prepared by procedures analogous to those used for Compound 1, starting from 2-amino-5-chlorobenzoic acid.

$^1$H-NMR (300 MHz, CDCl$_3$), mixture of atropisomers, δ: 0.94 & 1.11 (m, 9H), 2.3–2.6 (m, 4H), 2.75–3.0 (m, 4H), 3.49 (m, 1H), 3.7–4.0 (m, 7H), 4.18 (m, 1H), 4.39 (m, 1H), 6.08 (m, 1H), 6.54 (m, 1H), 7.57 (m, 2H), 8.00 (m, 1H), 8.19 (s, 1H).

MS (ES+) m/z 543/545.

Compound 33

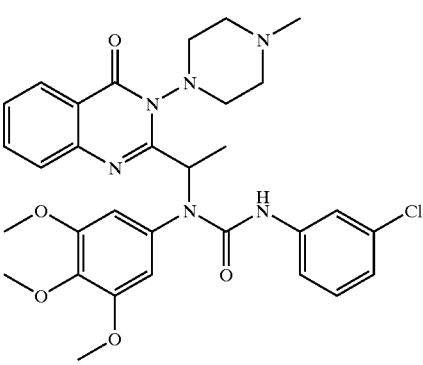

This compound was prepared by procedures analogous to those used for Compound 1.

$^1$H-NMR (300 MHz, CDCl$_3$), mixture of atropisomers, δ: 1.27 (m, 3H), 2.35–2.6 (m, 4H), 2.89 (m, 2H), 2.99 (m, 2H), 3.51 (m, 1H), 3.88 (s, 6H), 3.91 (s, 3H), 4.28 (m, 1H), 4.50 (m, 1H), 6.21 (q, J=7 Hz, 1H), 6.29 (s, 1H), 6.93 (m, 1H), 7.07 (m, 2H), 7.32 (m, 2H, with CHCl$_3$), 7.42 (m, 1H), 7.54 (m, 1H), 7.68 (m, 1H), 8.24 (d, J=8 Hz, 1H).

MS (ES+) m/z 607/609.

Compound 34

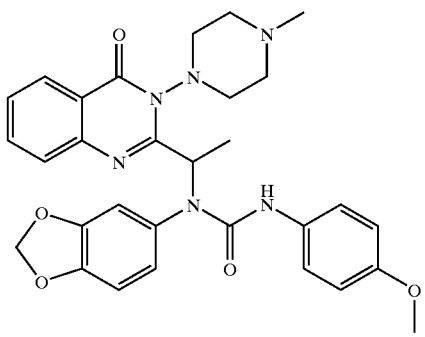

This compound was prepared by procedures analogous to those used for Compound 1.

$^1$H-NMR (300 MHz, CDCl$_3$), mixture of atropisomers, δ: 1.26 (d, J=7 Hz, 3H), 2.35–2.6 (m, 4H), 2.88 (m, 2H), 2.98 (m, 2H), 3.50 (m, 1H), 3.73 (s, 3H), 4.26 (m, 1H), 4.50 (m, 1H), 6.0–6.25 (m, 3H), 6.75 (d, J=9 Hz, 2H), 6.90 (d, J=8 Hz, 1H), 7.10 (d, J=9 Hz, 2H), 7.35 (m, 2H, with CHCl$_3$), 7.41 (m, 1H), 7.67 (m, 2H), 8.23 (d, J=8 Hz, 1H).

MS (ES+) m/z 557 (M$^+$+H); 579 (M$^+$+Na).

Compound 35

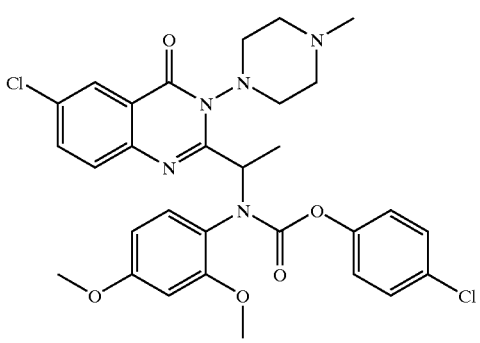

This compound was prepared by procedures analogous to those used for Compound 11, starting from 2-amino-5-chlorobenzoic acid, and condensing with 4-chlorophenyl chloroformate in the final step.

$^1$H-NMR (300 MHz, CDCl$_3$), mixture of atropisomers, δ: 1.21 & 1.56 (2d, J=7 Hz, 3H), 2.3–2.5 (m, 4H), 2.8–2.95 (m, 4H), 3.32 (m, 1H), 3.86 (s, 3H), 3.94 (s, 3H), 4.17 (m, 1H), 4.42 (m, 1H), 5.99 (q, J=7 Hz, 1H), 6.5–6.6 (m, 2H), 6.90 (d, J=9 Hz, 1H), 7.22 (m, 3H, with CHCl$_3$), 7.66 (m, 2H), 8.00 (d, J=8 Hz, 1H), 8.22 (m, 1H).

MS (ES+) m/z 612/614/616.

Compound 36

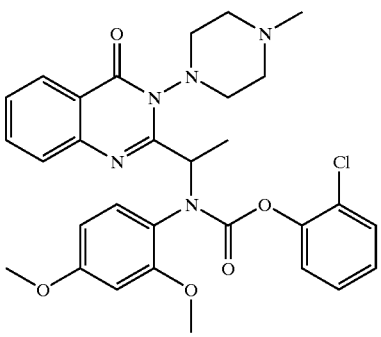

This compound was prepared by procedures analogous to those used for Compound 11, condensing with 2-chlorophenyl chloroformate in the final step.

$^1$H-NMR (300 MHz, CDCl$_3$), mixture of atropisomers, δ: 1.25 & 1.60 (2d, J=7 Hz, 3H), 2.3–2.5 (m, 4H), 2.8–2.95 (m, 4H), 3.32 (m, 1H), 3.86 (s, 3H), 3.95 (s, 3H), 4.15 (m, 1H), 4.45 (m, 1H), 5.96 (q, J=7 Hz, 1H), 6.57 (m, 2H), 7.05 (m, 2H), 7.15 (m, 1H), 7.29 (m, 1H, with CHCl$_3$), 7.43 (m, 1H), 7.74 (m, 2H), 8.25 (m, 2H).

MS (ES+) m/z 578/580.

Compound 37

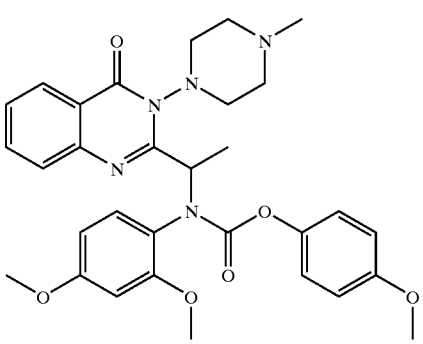

This compound was prepared by procedures analogous to those used for Compound 11, condensing with 4-methoxyphenyl chloroformate in the final step.

$^1$H-NMR (300 MHz, CDCl$_3$), mixture of atropisomers, δ: 1.22 (d, J=7 Hz, 3H), 2.3–2.5 (m, 4H), 2.8–2.95 (m, 4H), 3.35 (m, 1 H), 3.73 (s, 3H), 3.81 (s, 3H), 3.95 (s, 3H), 4.16 (m, 1H), 4.43 (m, 1H), 6.02 (q, J=7 Hz, 1H), 6.5–6.6 (m, 2H), 6.77 (d, J=9 Hz, 2H), 6.88 (d, J=9 Hz, 2H), 7.43 (m, 1H), 7.74 (m, 2H), 8.11 (d, J=8 Hz, 1H), 8.25 (m, 1H).

MS (ES+) m/z 574.

Compound 38

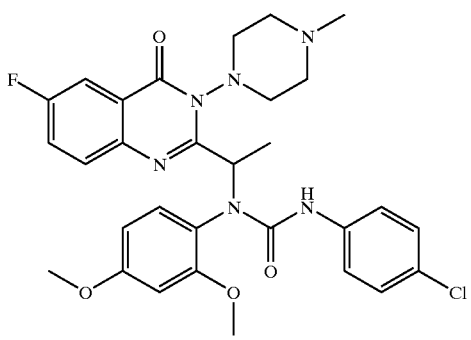

This compound was prepared by procedures analogous to those used for Example 1, starting from 2-amino-5-chlorobenzoic acid, and condensing with 4-chlorophenyl isocyanate in the final step.

¹H-NMR (300 MHz, CDCl₃), mixture of atropisomers, δ: 1.15 (d, J=6 Hz, 3H), 2.3–2.5 (m, 4H), 2.8–3.0 (m, 4H), 3.47 (m, 1H), 3.8–3.95 (m, 6H), 4.20 (m, 1H), 4.43 (m, 1H), 6.17 (m, 2H), 6.6 (m, 2H), 7.15 (m, 3H), 7.39 (m, 1H), 7.65 (m, 1H), 7.87 (m, 1H). 8.15 (m, 1H).

MS (ES+) m/z 595/597 (M+H).

Compound 39

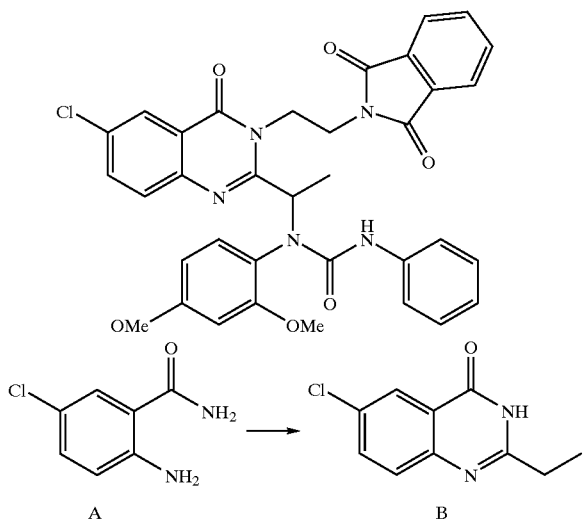

Compound A (3.0 g, 17.6 mmol) and propionic anhydride (2.5 mL, 19.3 mmol) were mixed and stirred at 90° C. under nitrogen for 20 min. Aqueous sodium hydroxide (2 M, 36 mL) was then added and the mixture was refluxed for 1 hr. After cooling, the reaction mixture was diluted with water and neutralized with 2 N HCl. The resulting precipitate was collected by filtration and dried, giving B (3.67 g, 100%).

¹H-NMR (300 MHz, CDCl₃) δ: 1.36 (t, J=8 Hz, 3H), 2.66 (q, J=7 Hz, 2H), 7.64 (m, 2H), 8.16 (d, J=2.4 Hz, 1H).

MS (ES+) m/z 209/211 (M+H).

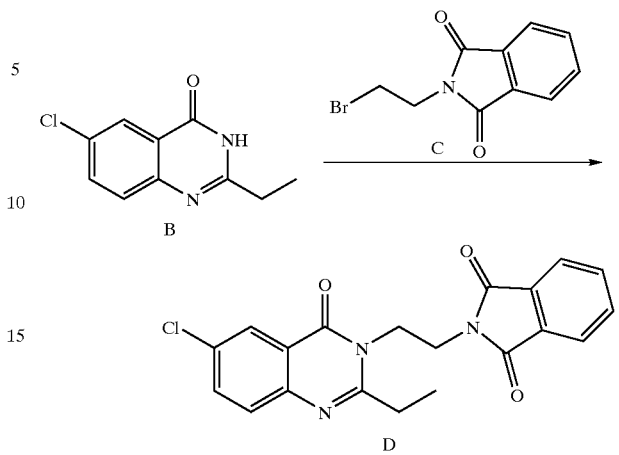

Compounds B (1.0 g, 4.8 mmol) and C (1.58 g, 6.2 mmol) were dissolved in DMF (50 mL). Freshly crushed potassium carbonate (1.3 g, 9.6 mmol) was added and the mixture was then stirred at 70° C. under nitrogen for 24 hr. The reaction mixture was diluted with water and extracted with ethyl acetate three times. The organic extracts were washed with brine and concentrated. The residue was purified by silica gel column chromatography (50% hexanes/50% ethyl acetate to 100% ethyl acetate), to give D (0.66 g, 36%).

¹H-NMR (300 MHz, CDCl₃) δ: 1.37 (t, J=7.2 Hz, 3H), 2.86 (q, J=7.2 Hz, 2H), 4.10 (t, J=6 Hz, 2H), 4.42 (t, J=6 Hz, 2H), 7.58 (m, 1H), 7.65 (m, 1H), 7.74 (m, 2H), 7.84 (m, 2H), 8.15 (d, J=2.4 Hz, 1H).

MS (ES+) m/z 382/384 (M+H).

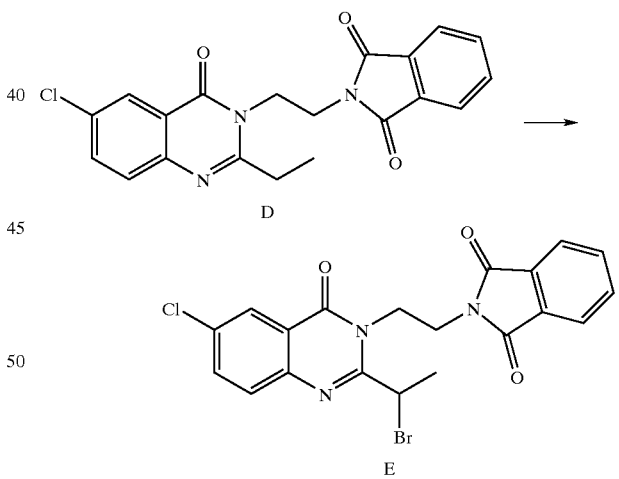

Compound D (0.66 g, 1.7 mmol) and sodium acetate (0.14 g, 1.7 mmol) were dissolved in acetic acid (20 mL) and warmed to 60° C. A solution of bromine (0.089 mL, 1.7 mmol) in acetic acid (5 mL) was added dropwise. The mixture was stirred at the same temperature for 2 hr. After cooling, the mixture was poured into ice-water with stirring. The precipitate was collected by filtration and dried, to give E (0.55 g, 69%).

¹H-NMR (300 MHz, CDCl₃), mixture of rotamers, δ: 1.54 & 2.09 (2m, 3H), 3.97 (m, 1H), 4.2 (m, 2H), 4.85 (m, 1H), 5.17 (m, 1H), 7.6–7.9 (m, 6H), 8.17 (s, 1H).

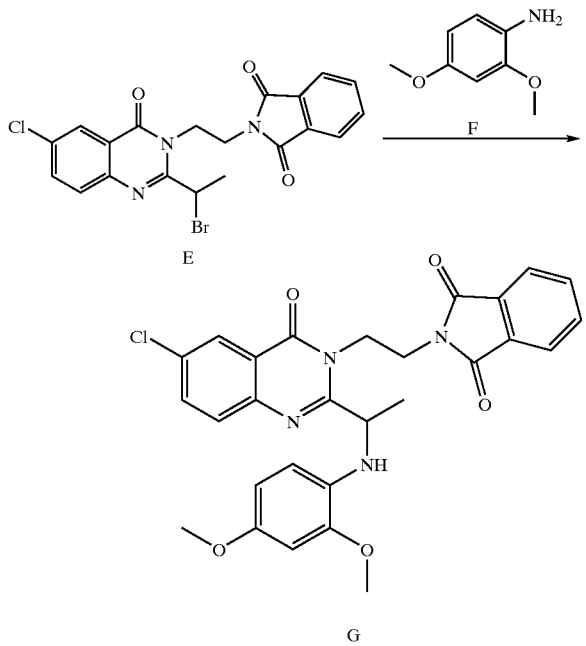

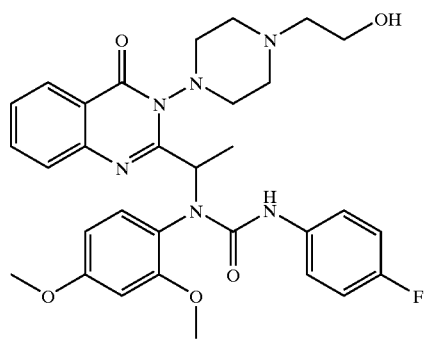

Compound G (0.46 g, 0.86 mmol) was dissolved in 1,2-dichloroethane (5 mL) and phenyl isocyanate (0.12 mL, 1.12 mmol) was added. The mixture was stirred at 40° C. for 16 hr and concentrated. The residue was purified by silica gel column chromatography (50% hexanes/50% ethyl acetate to 100% ethyl acetate) to give Compound 39 (0.37 g, 66%) as a yellow foam.

$^1$H-NMR (300 MHz, CDCl$_3$), mixture of atropisomers, δ: 1.35 & 1.57 (d, J=5 Hz, 3H), 3.04 & 3.79 & 3.86 (3s, 6H), 4.22 & 4.60 & 4.81 & 5.06 (4m, 4H), 5.92 & 6.1–6.2 & 6.3 & 6.52 & 6.59 (5m, 4H), 7.00 & 7.1–7.3 (2m, 5H, with CDCl$_3$), 7.55 & 7.68 & 7.78 (3m, 6H), 7.96 & 8.04 (2s, 1H).

MS (ES+) m/z 652/654.

Compound 40

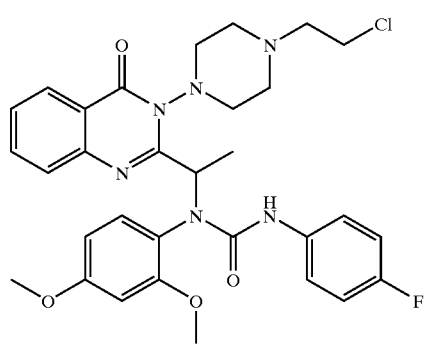

Compounds E (0.71 g, 1.5 mmol) and F (0.26 g, 1.7 mmol) were suspended in DMF (20 mL). Freshly crushed potassium carbonate (0.24 g, 1.7 mmol) was added and the mixture was then stirred at 80° C. under nitrogen for 16 hr. The reaction mixture was diluted with water and extracted three times with ethyl acetate. The organic extracts were washed with brine and concentrated. The residue was purified by silica gel column chromatography (50% hexanes/ 50% ethyl acetate to 100% ethyl acetate), to give G (0.46 g, 57%) as an orange solid.

$^1$H-NMR (300 MHz, CDCl$_3$), mixture of rotamers, δ: 1.50 (d, J=6.3 Hz, 3H), 3.6–3.9 (m, 7H), 4.1 (m, 2H), 4.40 (m, 1H), 4.60 (m, 1H), 4.80 (m, 1H), 6.3–6.5 (m, 3H), 6.65 (m, 2H), 7.65 (m, 4H), 8.15 (m, 1H).

MS (ES+) m/z 533/535.

This compound was prepared by procedures analogous to those used for Compound 3, condensing with 4-fluorophenyl isocyanate in the final step.

$^1$H-NMR (300 MHz, CDCl$_3$), mixture of atropisomers, δ: 1.18 (br s, 3H), 2.3–2.6 (m, 3H), 2.8–3.0 (m, 4H), 3.50 (m, 1H), 3.62 (m, 2H), 3.87 (s, 6H), 4.20 (m, 1H), 4.40 (m, 1H), 6.15 (m, 2H), 6.60 (m, 2H), 6.95 (m, 2H), 7.17 (m, 2H), 7.41 (m, 1H), 7.62 (m, 2H), 8.21 (d, J=8 Hz, 1H).

MS (ES+) m/z 591 (M$^+$+H).

Compound 41

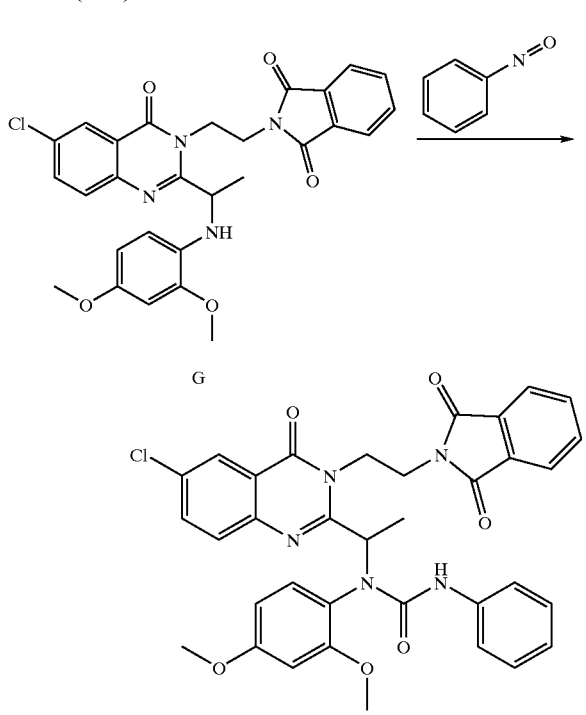

Compound 40 (53 mg) was stirred slowly with polymer-supported triphenylphosphine (150 mg) in carbon tetrachloride (1 mL) and THF (5 mL) at 80° C. for 2 hrs. An additional 450 mg polymer-supported triphenylphosphine in carbon tetrachloride (1 mL) was added and the mixture was heated for a further 2 hrs to achieve complete consumption of the starting material. Ethyl acetate (40 mL) was added, and the mixture was filtered through diatomaceous earth and concentrated. Purification by radial chromatography on silica gel (dichloromethane as eluant) gave the product (30 mg).

$^1$H-NMR (300 MHz, CDCl$_3$), mixture of atropisomers, δ: 1.18 (br s, 3H), 2.4–2.8 (m, 1H), 2.8–3.0 (m, 7H), 3.45 &

3.62 (2m, 2H), 3.82 (s, 6H), 4.20 (m, 1H), 4.40 (m, 1H), 6.10 (m, 2H), 6.59 (m, 2H), 6.89 (m, 2H), 7.15 (m, 2H), 7.41 (m, 1H), 7.62 (m, 2H), 8.21 (d, J=8 Hz, 1H).

MS (ES+) m/z 609/611 (M$^+$+H).

Compound 42

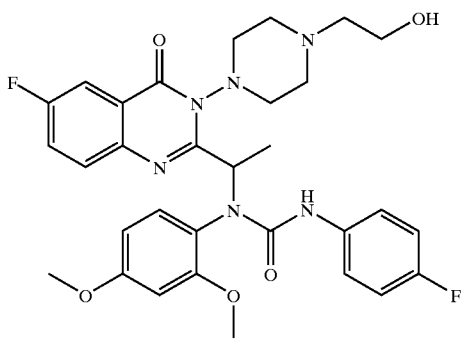

This compound was prepared by procedures analogous to those used for Compound 3, starting from 2-amino-5-fluorobenzoic acid, and condensing with 4-fluorophenyl isocyanate in the penultimate step.

$^1$H-NMR (300 MHz, CDCl$_3$), mixture of atropisomers, δ: 1.18 (br s, 3H), 2.5–2.8 (m, 3H), 2.8–3.0 (m, 4H), 3.50 (m, 1H), 3.65 (m, 2H), 3.85 (s, 6H), 4.20 (m, 1H), 4.40 (m, 1H), 6.15 (m, 2H), 6.60 (m, 2H), 6.95 (m, 2H), 7.17 (m, 1H), 7.39 (m, 1H), 762 (m, 1H), 7.85 (m, 1H), 8.21 (m, 1H).

MS (ES+) m/z 609 (M$^+$+H).

Compound 43

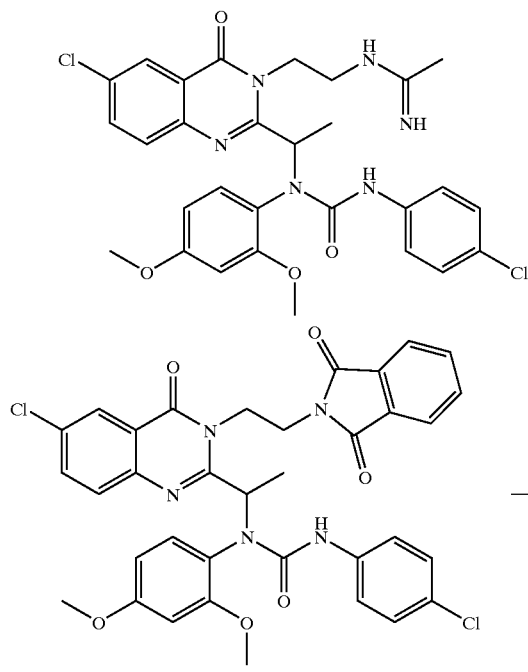

-continued

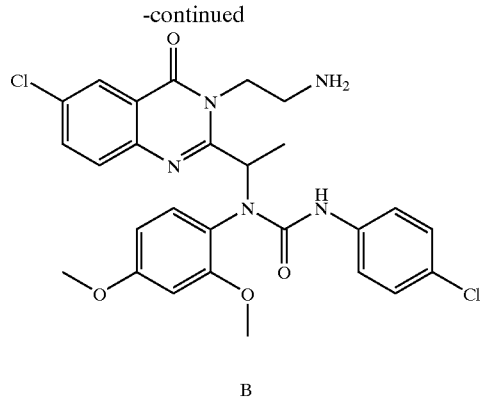

Compound A, made in a manner analogous to Compound 39, (250 mg, 0.36 mmol) and hydrazine hydrate (0.180 mL, 3.6 mmol) were dissolved in ethanol (200 mL, due to low solubility) and refluxed under nitrogen for 24 h. The reaction mixture was concentrated and triturated with water. The residue was purified by silica gel column chromatography (5% methanol in dichloromethane), to give B (200 mg, 100%) as a white solid.

Compound B (60 mg, 0.11 mmol) was stirred with ethyl acetimidate hydrochloride (16 mg, 0.13 mmol) and triethylamine (23 μL, 0.16 mmol) in THF (5 mL) at room temperature overnight. More ethyl acetimidate hydrochloride (27 mg, 0.21 mmol) and triethylamine (30 μL, 0.26 mmol) were added. After a further 24 hrs, the reaction was diluted with ethyl acetate and washed with brine. After drying with sodium sulfate, filtration and evaporation, Compound 43 (61 mg) was obtained as an oil.

$^1$H-NMR (300 MHz, CDCl$_3$), mixture of atropisomers, δ: 1.2 & 1.55 (2m, 3H), 2 28 (s, 3H), 3.02 & 3.8 (2m, 6H), 4.22 & 4.60 & 4.8 & 5.1 (4m, 4H), 5.58 & 6.1–6.4 & 6.5–6.7 (3m, 4H), 6.9 & 7.0–7.3 (2m, 4H, with CDCl$_3$), 7.5–7.8 (m, 2H), 7.90 & 8.15 (2m, 1H).

MS (ES+) m/z 597/599/601.

Compound 44

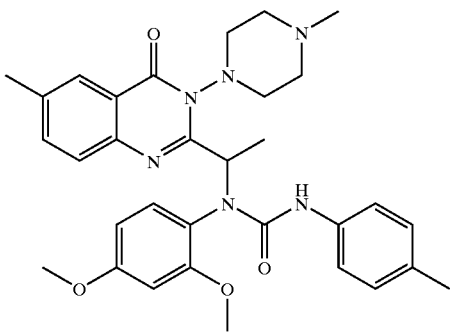

This compound was prepared by procedures analogous to those used for Compound 1, starting from 2-amino-5-methylbenzoic acid, and condensing with p-toluyl chloroformate in the final step.

$^1$H-NMR (200 MHz, CDCl$_3$), mixture of atropisomers, δ: 1.1–1.4 (m, 3H), 2.25 (s, 3H), 2.3–2.5 (m, 7H), 2.8–2.95 (m, 4H), 3.45 (m, 1H), 3.9 (s, 6H), 4.2 (m, 1H), 4.4 (m, 1H), 6.15 (m, 2H (includes NH)), 6.6 (m, 2H), 6.95–7.2 (m, 4H), 7.5 (m, 2H), 8.0–8.2 (m, 1H).

MS (ES+) m/z 571.7 (M+H$^+$).

Compound 45

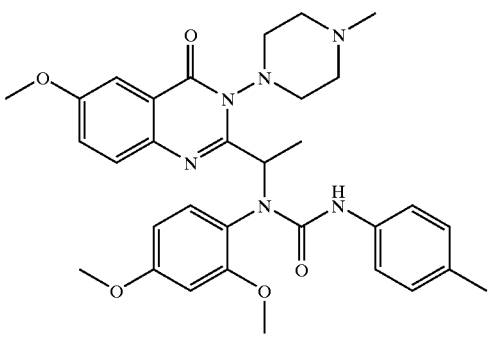

This compound was prepared by procedures analogous to those used for Compound 1, starting from 2-amino-5-methoxybenzoic acid, and condensing with p-tolyl chloroformate in the final step.

$^1$H-NMR (200 MHz, CDCl$_3$), mixture of atropisomers, δ: 1.1–1.4 (m, 3H), 2.25 (s, 3H), 2.3–2.5 (m, 4H), 2.7–3.0 (m, 4H), 3.5 (m, 1H), 3.9 (s, 9H), 4.2 (m, 1H), 4.4 (m, 1H), 6.15 (m, 2H (includes NH)), 6.6 (m, 2H), 6.95–7.2 (m, 5H), 7.6 (m, 2H), 8.2 (m, 1H).

MS (ES+) m/z 587 (M+H$^+$).

Table 1 lists the IUPAC names of the above compounds.

TABLE 1

| Cmpd | IUPAC Name |
| --- | --- |
| 1 | 3-(3-Chloro-phenyl)-1-(2,4-dimethoxy-phenyl)-1-{1-[3-(4-methyl-piperazin-1-yl)-4-oxo-3,4-dihydro-quinazolin-2-yl]-ethyl}-urea |
| 2 | Acetic acid 2-[4-(2-{1-[3-(3-chloro-phenyl)-1-(2,4-dimethoxy-phenyl)-ureido]-ethyl}-4-oxo-4H-quinazolin-3-yl)-piperazin-1-yl]-ethylester |
| 3 | 3-(3-Chloro-phenyl)-1-(2,4-dimethoxy-phenyl)-1-(1-{3-[4-(2-hydroxy-ethyl)-piperazin-1-yl]-4-oxo-3,4-dihydro-quinazolin-2-yl}-ethyl)-urea |
| 4 | 3-(3-Chloro-phenyl)-1-(4-methoxy-phenyl)-1-{1-[3-(4-methyl-piperazin-1-yl)-4-oxo-3,4-dihydro-quinazolin-2-yl]-ethyl}-urea |
| 5 | 3-(3-Chloro-phenyl)-1-(4-methoxy-2-methyl-phenyl)-1-{1-[3-(4-methyl-piperazin-1-yl)-4-oxo-3,4-dihydro-quinazolin-2-yl]-ethyl}-urea |
| 6 | 3-(2-Chloro-phenyl)-1-(2,4-dimethoxy-phenyl)-1-{1-[3-(4-methyl-piperazin-1-yl)-4-oxo-3,4-dihydro-quinazolin-2-yl]-ethyl}-urea |
| 7 | 3-(4-Chloro-phenyl)-1-(2,4-dimethoxy-phenyl)-1-{1-[3-(4-methyl-piperazin-1-yl)-4-oxo-3,4-dihydro-quinazolin-2-yl]-ethyl}-urea |
| 8 | 1-(2,4-Dimethoxy-phenyl)-1-{1-[3-(4-methyl-piperazin-1-yl)-4-oxo-3,4-dihydro-quinazolin-2-yl)-ethyl}-3-phenyl-urea |
| 9 | 1-(2,4-Dimethoxy-phenyl)-3-(2-methoxy-phenyl)-1-{1-[3-(4-methyl-piperazin-1-yl)-4-oxo-3,4-dihydro-quinazolin-2-yl]-ethyl}-urea |
| 10 | 4-Chloro-N-(2,4-dimethoxy-phenyl)-N-{1-[3-(4-methyl-piperazin-1-yl)-4-oxo-3,4-dihydro-quinazolin-2-yl]-ethyl}-benzenesulfonamide |
| 11 | (2,4-Dimethoxy-phenyl)-{1-[3-(4-methyl-piperazin-1-yl)-4-oxo-3,4-dihydro-quinazolin-2-yl]-ethyl}-carbamic acid phenyl ester |
| 12 | 3-(4-Chloro-phenyl)-1-(4-methoxy-phenyl)-1-{1-[3-(4-methyl-piperazin-1-yl)-4-oxo-3,4-dihydro-quinazolin-2-yl]-ethyl}-urea |
| 13 | 1-(2,4-Dimethoxy-phenyl)-3-(4-fluoro-phenyl)-1-{1-[3-(4-methyl-piperazin-1-yl)-4-oxo-3,4-dihydro-quinazolin-2-yl]-ethyl}-urea |
| 14 | 1-(2,4-Dimethoxy-phenyl)-1-{1-[3-(4-methyl-piperazin-1-yl)-4-oxo-3,4-dihydro-quinazolin-2-yl]-ethyl}-3-p-tolyl-urea |
| 15 | 1-(2,4-Dimethoxy-phenyl)-3-(4-methoxy-phenyl)-1-{1-[3-(4-methyl-piperazin-1-yl)-4-oxo-3,4-dihydro-quinazolin-2-yl]-ethyl}-urea |
| 16 | 2-Chloro-N-(2,4-dimethoxy-phenyl)-N-{1-[3-(4-methyl-piperazin-1-yl)-4-oxo-3,4-dihydro-quinazolin-2-yl]-ethyl}-benzenesulfonamide |
| 17 | (2,4-Dimethoxy-phenyl)-{1-[3-(4-methyl-piperazin-1-yl)-4-oxo-3,4-dihydro-quinazolin-2-yl]-ethyl}-carbamic acid 4-chlorophenyl ester |
| 18 | 1-Benzo[1,3]dioxol-5-yl-3-(3-chloro-phenyl)-1-{1-[3-(4-methyl-piperazin-1-yl)-4-oxo-3,4-dihydro-quinazolin-2-yl]-ethyl}-urea |
| 19 | (2,4-Dimethoxy-phenyl)-{1-[3-(4-methyl-piperazin-1-yl)-4-oxo-3,4-dihydro-quinazolin-2-yl]-ethyl}-carbamic acid p-tolyl ester |
| 20 | 1-(2,4-Dimethoxy-phenyl)-1-{1-[3-(4-methyl-piperazin-1-yl)-4-oxo-3,4-dihydro-quinazolin-2-yl]-ethyl}-3-m-tolyl-urea |
| 21 | 1-(2,4-Dimethoxy-phenyl)-3-(3-fluoro-phenyl)-1-{1-[3-(4-methyl-piperazin-1-yl)-4-oxo-3,4-dihydro-quinazolin-2-yl)-ethyl}-urea |
| 22 | 3-(3-Chloro-phenyl)-1-(2,4-dimethoxy-phenyl)-1-{1-[3-(1-methyl-piperidin-4-yl)-4-oxo-3,4-dihydro-quinazolin-2-yl]-ethyl}-urea |
| 23 | 1-{1-[6-Chloro-3-(4-methyl-piperazin-1-yl)-4-oxo-3,4-dihydro-quinazolin-2-yl]-ethyl}-3-(3-chloro-phenyl)-1-(2,4-dimethoxy-phenyl)-urea |
| 24 | 1-{1-[6-Chloro-3-(4-methyl-piperazin-1-yl)-4-oxo-3,4-dihydro-quinazolin-2-yl]-ethyl}-1-(2,4-dimethoxy-phenyl)-3-phenyl-urea |
| 25 | 1-{1-[6-Chloro-3-(4-methyl-piperazin-1-yl)-4-oxo-3,4-dihydro-quinazolin-2-yl]-ethyl}-1-(2,4-dimethoxy-phenyl)-3-(4-methoxy-phenyl)-urea |
| 26 | N-(2,4-Dimethoxy-phenyl)4-methyl-N-{1-[3-(4-methyl-piperazin-1-yl)-4-oxo-3,4-dihydro-quinazolin-2-yl)-ethyl}-benzamide |
| 27 | 3-Chloro-N-(2,4-dimethoxy-phenyl)-N-{1-[3-(4-methyl-piperazin-1-yl)-4-oxo-3,4-dihydro-quinazolin-2-yl)-ethyl}-benzamide |
| 28 | 4-Chloro-N-(2,4-dimethoxy-phenyl)-N-{1-[3-(4-methyl-piperazin-1-yl)-4-oxo-3,4-dihydro-quinazolin-2-yl)-ethyl}-benzamide |
| 29 | 2-Chloro-N-(2,4-dimethoxy-phenyl)-N-{1-[3-(4-methyl-piperazin-1-yl)-4-oxo-3,4-dihydro-quinazolin-2-yl)-ethyl}-benzamide |
| 30 | N-(2,4-Dimethoxy-phenyl)-4-methoxy-N-{1-[3-(4-methyl-piperazin-1-yl)-4-oxo-3,4-dihydro-quinazolin-2-yl]-ethyl}-benzamide |
| 31 | 1-Benzo[1,3]dioxol-5-yl-3-(4-chloro-phenyl)-1-{1-[3-(4-methyl-piperazin-1-yl)-4-oxo-3,4-dihydro-quinazolin-2-yl]-ethyl}-urea |

TABLE 1-continued

| Cmpd | IUPAC Name |
|---|---|
| 32 | 1-{1-[6-Chloro-3-(4-methyl-piperazin-1-yl)-4-oxo-3,4-dihydro-quinazolin-2-yl]-ethyl}-1-(2,4-dimethoxy-phenyl)-3-isopropyl-urea |
| 33 | 3-(3-Chloro-phenyl)-1-{1-[3-(4-methyl-piperazin-1-yl)-4-oxo-3,4-dihydro-quinazolin-2-yl]-ethyl}-1-(3,4,5-trimethoxy-phenyl)-urea |
| 34 | 1-Benzo[1,3]dioxol-5-yl-3-(4-methoxy-phenyl)-1-{1-[3-(4-methyl-piperazin-1-yl)-4-oxo-3,4-dihydro-quinazolin-2-yl]-ethyl}-urea |
| 35 | {1-[6-Chloro-3-(4-methyl-piperazin-1-yl)-4-oxo-3,4-dihydro-quinazolin-2-yl]-ethyl}-(2,4-dimethoxy-phenyl)-carbamic acid 4-chloro-phenyl ester |
| 36 | (2,4-Dimethoxy-phenyl)-{1-[3-(4-methyl-piperazin-1-yl)-4-oxo-3,4-dihydro-quinazolin-2-yl]-ethyl}-carbamic acid 2-chloro-phenyl ester |
| 37 | (2,4-Dimethoxy-phenyl)-{1-[3-(4-methyl-piperazin-1-yl)-4-oxo-3,4-dihydro-quinazolin-2-yl]-ethyl}-carbamc acid 4-methoxy-phenyl ester |
| 38 | 3-(4-Chloro-phenyl)-1-(2,4-dimethoxy-phenyl)-1-{1-[6-fluoro-3-(4-methyl-piperazin-1-yl)-4-oxo-3,4-dihydro-quinazolin-2-yl]-ethyl}-urea |
| 39 | 1-(1-{6-Chloro-3-[2-(1,3-dioxo-1,3-dihydro-isoindol-2-yl)-ethyl]-4-oxo-3,4-dihydro-quinazolin-2-yl}-ethyl)-1-(2,4-dimethoxy-phenyl)-3-phenyl-urea |
| 40 | 1-(2,4-Dimethoxy-phenyl)-3-(4-fluoro-phenyl)-1-(1-{3-[4-(2-hydroxy-ethyl)-piperazin-1-yl]-4-oxo-3,4-dihydro-quinazolin-2-yl}-ethyl)-urea |
| 41 | 1-(1-{3-[4-(2-Chloro-ethyl)-piperazin-1-yl]-4-oxo-3,4-dihydro-quinazolin-2-yl}-ethyl)-1-(2,4-dimethoxy-phenyl)-3-(4-fluoro-phenyl)-urea |
| 42 | 1-(2,4-Dimethoxy-phenyl)-1-(1-{6-fluoro-3-[4-(2-hydroxy-ethyl)-piperazin-1-yl]-4-oxo-3,4-dihydro-quinazolin-2-yl}-ethyl)-3-(4-fluoro-phenyl)-urea |
| 43 | N-[2-(6-Chloro-2-{1-[3-(4-chloro-phenyl)-1-(2,4-dimethoxy-phenyl)-ureido]-ethyl}-4-oxo-4H-quinazolin-3-yl)-ethyl]-acetamidine |
| 44 | 1-(2,4-Dimethoxy-phenyl)-1-{1-[6-methyl-3-(4-methyl-piperazin-1-yl)-4-oxo-3,4-dihydro-quinazolin-2-yl]-ethyl}-3-p-tolyl-urea |
| 45 | 1-(2,4-Dimethoxy-phenyl)-1-{1-[6-methoxy-3-(4-methyl-piperazin-1-yl)-4-oxo-3,4-dihydro-quinazolin-2-yl]-ethyl}-3-p-tolyl-urea |

Pharmaceutical Compositions and Modes of Administration

An efflux pump inhibitory compound or compounds of this invention, or derivatives thereof, and an anti-fungal agent or agents can be administered to a patient serially or simultaneously. If serial administration is contemplated, the presently preferred approach is to administer the compound of this invention first. This permits the compound to inhibit the efflux pump(s) of the target fungal cells before the anti-fungal agent is administered, which should result in a substantially lower dosage of the anti-fungal agent being required since the fungal cells will not be able to excrete the agent. By "simultaneous" administration is meant that a compound of this invention and an anti-fungal agent are administered to a patient at essentially the same time. This can be accomplished by administering the compound herein and the anti-fungal agent separately, as in the case of two separate tablets or capsules, separate iv drips, or separate injections administered one immediately after the other. In a presently preferred embodiment, "simultaneously" means that the compound of this invention is prepared as a homogeneous composition with an anti-fungal agent and that composition is administered to the patient.

A compound of the present invention, a prodrug thereof or a physiologically acceptable salt of either the compound or its prodrug, can be administered as such to a patient or it can be administered in pharmaceutical compositions in which the compounds are mixed with suitable carriers or excipient(s). Techniques for formulation and administration of drugs may be found in *Remington's Pharmacological Sciences,* Mack Publishing Co., Easton, Pa., latest edition.

Suitable routes of administration include, without limitation, oral, rectal, vaginal, transmucosal, intramuscular, subcutaneous, intramedullary, intrathecal, direct intraventricular, intravenous, intravitreal, intraperitoneal, intranasal, or intraocular. The presently preferred routes of administration are oral and parenteral.

Alternatively, one may administer the compound in a localized topical rather than systemic manner. That is, the homogeneous composition of a compound herein and an anti-fungal agent can be applied directly to the surface of an infected area or injected directly into the infection.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Such pharmaceutical compositions are formulated in conventional manner and may include one or more pharmaceutically acceptable carriers, excipients and/or auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer.

For transmucosal administration, penetrants appropriate to the barrier to be permeated are used in the formulation. Such penetrants are generally known in the art.

For oral administration, the compounds can be formulated by combining the active ingredients with pharmaceutically acceptable carriers well known in the art. Such carriers enable the compounds of the invention to be formulated as tablets, pills, lozenges, dragees, capsules, liquids, gels, syrups, slurries, suspensions and the like, suitable for oral ingestion. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethylcellulose, sodium carboxymethyl-cellulose, and/or polyvinylpyrrolidone (PVP). Disintegrating agents may also be added, such as cross-linked polyvinyl pyrrolidone, agar, or alginic acid. A salt such as sodium alginate may also be used.

Dragee cores are often provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings to identify the particular compounds in that composition and/or their dosages.

Pharmaceutical formulations which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage may be controlled by providing a valve that delivers a metered amount. Capsules and cartridges of, for example, gelatin for use in an inhaler or insufflator may be formulated containing a powder mix of the compound and a suitable powder base such as lactose or starch.

The compounds may also be formulated for parenteral administration. Formulations for parenteral injection may be in unit dosage form, e.g., in single-dose ampoules, or in multi-dose containers. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Or, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water.

The compounds may also be formulated in rectal compositions such as suppositories or retention enemas, using, e.g., conventional suppository bases such as cocoa butter or other glycerides.

The compounds may also be formulated as depot preparations. Such long acting formulations may be administered by implantation (for example, subcutaneously or intramuscularly) or by intramuscular injection. A compound of this invention may be formulated for this route of administration with suitable hydrophobic materials (for instance, in an emulsion with a pharmacologically acceptable oil), with ion exchange resins, or as a sparingly soluble derivative such as, without limitation, a sparingly soluble salt.

Delivery systems for hydrophobic pharmaceutical compounds include, without limitation, liposomes and emulsions. These are well known examples of delivery vehicles or carriers for hydrophobic drugs. In addition, certain organic solvents such as dimethylsulfoxide may be employed, although often at the cost of greater toxicity.

The compounds may be delivered using a sustained-release system, such as semipermeable matrices of solid hydrophobic polymers. Sustained-release materials and methods are well known to those skilled in the art. Sustained-release capsules may, depending on their chemical nature, release the compounds for a relatively short period of time, a few days perhaps even a few hours, or over very long periods of time such as 100 days or more.

The pharmaceutical compositions herein may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Dosage

Determination of a dosage that will result in a therapeutically effective amount of a fungal agent and compound of this invention being delivered to a patient will require assessment of such parameters as, without limitation, the age, gender, weight and physical condition of the patient as well as the severity of the infection, route of administration and response to previous treatments, if any. All of these are well within the knowledge and expertise of the treating physician.

In addition to the above considerations, it will be understood that the maximum permissible dose of known anti-fungal agents can be readily found in the pharmacological literature. The effect of various quantities of a compound of this invention on the amount of an anti-fungal agent required to treat a fungal infection can be found in this disclosure or, if other anti-fungal agents and/or other compounds herein are selected for use, can be determined without undue experimentation using the methods described herein.

While it may on occasion be desirable, even necessary, to treat a patient with massive doses of an anti-fungal agent and a compound of this invention, generally, it is preferred to use the least amount of the anti-fungal compound and of the compound herein that achieves the desired therapeutic or prophylactic effect. This determination is likewise well within the capability of the treating physician.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a fungal infections caused by particular species of fungus and the like.

Biological Activity

All of the compounds, save Compound 39, were tested as their mesylate salts.

The activity of test compounds of this invention in combination with an anti-fungal were assessed using a checkerboard assay and the broth microdilution protocol recommended by NCCLS Documents M27-A, Vol. 17, No. 9, June 1997, entitled, "Reference Method for Broth Dilution Anti-fungal Susceptibility Testing of Yeasts, Approved Standard," and NCCLS Document M38-P, Vol. 18, No. 13, November 1998, entitled, "Reference Method for Broth Dilution Anti-fungal Susceptibility Testing of Conidium-Forming Filamentous Fungi; Proposed Standard." The test organisms used are *Candida albicans* YEM15 (over-expressing the CDR1 and CDR2 pumps), *C. glabrata* YEM19 (over-expressing the CgCDR1 and CgCDR2 pumps), and clinical isolates of *C. tropicalis, C. krusei, C. parapsilosis* and *A. fumigatus*.

In this assay, multiple dilutions of a known anitfungal and a compound of this invention, are tested alone and in combination at concentrations equal to, above and below the MIC, minimum inhibitory concentration, of the anti-fungal. Unless specifically stated to be otherwise, MIC's are usually reported as the amount of a compound necessary to achieve 80% of the maximum effect possible with that compound. Thus, for example, for an antifungal agent it would be the concentration of the agent that inhibits 80% of the fungal cells contacted. For instance, the MICs of fluconazole against YEM15 and YEM19 are 64 and 128 ug/ml respectively. The compounds of this invention, most of which are shown to have little or no intrinsic anti-fungal activity, are tested at concentration of from about 4 to about 32 µg/ml.

Stock solutions of the test compounds are prepared at a concentration of 4–128 µg/ml. Stock solutions are then diluted, according to the needs of a particular assay, in RPMI-1640 with MOPS buffer at 165 mM L-glutamine (Angus Buffers & Biochemicals, catalog no. R63165). Stock solutions can be stored at 4° C. Fluconazole is solubilized according to the instructions of the manufacturers, at a concentration of 10 mg/ml in 100% DMSO. It is then further diluted in RPMI.

The checkerboard assay is normally performed on microtiter plates. Serial dilutions of the anti-fungal are placed in wells horizontally across the plate resulting in each well in any column of wells having the same concentration of the anti-fungal. The test compound is serially diluted in each column of wells resulting in the rows of wells each containing the same concentration of the test compound. Thus, each well in the array contains a unique combination of anti-fungal and test compound concentrations. Test compounds are examined one per plate.

The assay is performed in RPMI using a final fungal inoculum of 1 to $5 \times 10^3$ CFU/ml (from an early-log phase culture). Microtiter plates are incubated for 48 h at 35+ C. and are read using a microtiter plate reader (Molecular Devices) at 650 nm.

Tables 2–5 show that potentiation of an anti-fungal agent, as manifested by a reduction in the MIC of the anti-fungal, in the presence, as contrasted to the absence, of an efflux pump inhibitor of this invention.

TABLE 2

Potentiation of fluconazole vs. *C. albicans**

| Compound Number | MIC (µg/ml) | MPC$_8$ (µg/ml)** |
|---|---|---|
| 1 | >32 | 0.125 |
| 2 | >32 | <0.5 |
| 3 | >32 | 0.03 |
| 4 | 32 | 2 |
| 5 | 32 | 4 |
| 6 | >32 | 4 |
| 7 | >32 | 1 |
| 8 | >32 | 2 |
| 9 | >32 | 16 |
| 10 | 32 | 32 |
| 12 | >32 | 8 |
| 13 | >32 | 4 |
| 14 | >32 | 2 |
| 15 | >32 | 16 |
| 16 | >32 | 32 |
| 17 | >32 | 8 |
| 18 | 32 | 0.125 |
| 19 | >32 | 16 |
| 20 | >32 | 0.5 |
| 21 | >32 | 0.25 |
| 22 | >32 | 16 |
| 23 | >32 | 0.25 |
| 24 | >32 | 0.125 |
| 25 | >32 | 1 |
| 26 | >32 | 4 |
| 27 | >32 | 8 |

TABLE 2-continued

Potentiation of fluconazole vs. *C. albicans**

| Compound Number | MIC (µg/ml) | MPC$_8$ (µg/ml)** |
|---|---|---|
| 28 | >32 | 4 |
| 29 | >32 | 4 |
| 30 | >32 | 16 |
| 31 | >32 | 2 |
| 32 | >32 | 4 |
| 33 | >32 | 8 |
| 34 | >32 | 8 |
| 35 | >32 | 4 |
| 36 | >32 | 16 |
| 37 | >32 | 32 |
| 38 | >32 | 0.5 |
| 39 | 16 | ≦0.03 |
| 40 | >32 | 2 |
| 41 | >32 | 8 |
| 42 | >32 | 1 |
| 43 | >32 | 4 |
| 44 | >32 | 0.25 |
| 45 | >32 | 1 |

*Strain YEM15, over-expressing CDR1 and CDR2 efflux pumps MIC = concentration of fluconazole alone that causes a 80% inhibition the growth/proliferation of fungal cells
**MPC$_8$ = concentration of efflux pump inhibitor necessary to reduce the fluconazole MIC 8-fold

TABLE 3

Potentiation of fluconazole vs. *C. glabrata**

| Compound Number | MIC (µg/ml) | MPC$_8$ (µg/ml) |
|---|---|---|
| 1 | >32 | 2 |
| 2 | >32 | 2 |
| 3 | >32 | 1 |
| 4 | >32 | 32 |
| 6 | >32 | 2 |
| 8 | >32 | 8 |
| 11 | >32 | 32 |
| 12 | >32 | 16 |
| 13 | >32 | 4 |
| 14 | >32 | 2 |
| 15 | >32 | 2 |
| 17 | >32 | 16 |
| 18 | >32 | 32 |
| 19 | >32 | 32 |
| 20 | >32 | 1 |
| 21 | >32 | 2 |
| 22 | >32 | 32 |
| 23 | >32 | 2 |
| 24 | >32 | 4 |
| 25 | >32 | 4 |
| 31 | >32 | 16 |
| 35 | >32 | 8 |
| 38 | >32 | 0.25 |
| 40 | >32 | 4 |
| 41 | >32 | 8 |
| 42 | >32 | 1 |
| 43 | >32 | 1 |
| 44 | >32 | 2 |
| 45 | >32 | 1 |

*Strain YEM19, over-expressing CgCDR1 and CgCDR2 efflux pumps
MIC = the concentration of fluconazole alone required to achieve 80% inhibition of the growth of the fungal cells.

TABLE 4

Potentiation of fluconazole vs. clinical isolates of *C. tropicalis, C. krusei,* and *C. parapsilosis*

| Cmpd. Number | Species | # isolates tested | $MIC_{50}$** – Flu only | $MIC_{50}$ Flu + FEPI | $MIC_{90}$ – Flu only | $MIC_{90}$ Flu + FEPI |
|---|---|---|---|---|---|---|
| 1* | C. tropicalis | 25 | 128 | 0.125 | >128 | 2 |
|  | C. krusei | 17 | 64 | 32 | >128 | >32 |
|  | C. parapasilosis | 10 | 1 | <0.03 | 4 | 0.25 |
| 3* | C. tropicalis | 11 | >128 | 0.25 | >128 | 8 |
|  | C. krusei | 11 | 64 | >32 | >128 | >32 |
|  | C. parapasilosis | 10 | 1 | <0.03 | 4 | 0.5 |

FEPI = fungal efflux pump inhibitor, i.e., a compound of this invention.
*concentration 16–32 μg/ml
**all MICs in μg/ml; $MIC_{50}$ is the concentration of fluconazole in combination with the indicated concentration of the FEPI that results in a 80% inhibition in the growth of the indicated fungal species. $MIC_{90}$ is the concentration of fluconazole in combination with the indicated concentration of the FEPI to achieve a 90% inhibition of the fungus.

TABLE 5

Potentiation of Posaconazole vs. *A. fumigatus**

| Compound Number | MIC (μg/ml) | $MPC_8$ (μg/ml) |
|---|---|---|
| 1 | >32 | 8–32 |

MIC = minimum inhibitor concentration of Posaconazole alone to achieve 80% inhibition of the growth/proliferation of *A. fumigatus* cells.
$MPC_8$ = concentration of efflux pump inhibitor to reduce MIC of Posaconazole 8-fold.
*15 strains; 2 wild type, 11 Itraconazole resistant, 2 clinical isolates overexpressing efflux pumps

CONCLUSION

The patents and publications referenced herein are indicative of the level of skill of those skilled in the art to which this invention pertains. All such patents and publications are incorporated by reference to the same extent as if each had been separately incorporated by reference.

While the above description describes particular embodiments and examples illustrating the invention, those skilled in the art will recognize that the invention may be practiced in a variety of alternative ways, for example, by potentiating a variety of other anti-fungal agents that exhibit an efflux pump resistance mechanism. All such variations are within the scope of this invention. Other embodiments of this invention are contained in the following claims.

What is claimed is:

1. A fungal efflux pump inhibitory compound having the chemical structure:

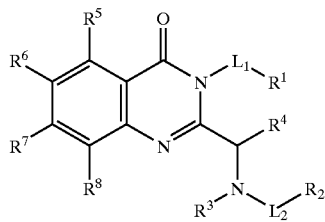

wherein:
  $L^1$ is selected from the group consisting of a single bond and $C_x^1$;

$R^1$ is selected from the group consisting of:
  ($C_3$–$C_7$)heteroalicyclic containing 1 nitrogen atom and 0 to 2 additional heteroatoms independently selected from the group consisting of nitrogen, oxygen and sulfur wherein the heteroalicyclic is substituted with one or more substituents independently selected from the group consisting of hydrogen, halo, hydroxy, $-C_x^2$, $=O$, $-OC_x^2$, $-C_x^2OC_x^3$, $-C_x^2OH$, $-C_x^2(halo)$, $-C_x^2OC(=O)C_x^3$, $-C_x^2NHC(=O)C_x^3$, $-C_x^2NHC(=NH)C_x^3$, $-NHC_x^2$, $-NC_x^2C_x^3$, $-C_x^2NH_2$, $-C_x^2NHC_x^3$, $-C_x^2NC_x^3C_x^4$ and $-C=C-C=C-$, wherein the end carbons of the group are covalently bonded to adjacent carbon atoms of the heteroalicyclic ring to form a carbocyclic ring, the adjacent carbon atoms of the heteroalicyclic being double-bonded to one another such that the carbocyclic ring formed is a phenyl group;
  $-C_x^2NHC(=NH)C_x^3$; $-C_x^2NC_x^3C(=NH)C_x^{13}$ and, $-C_x^2NHC(=O)C_x^3$;

$L^2$ is selected from the group consisting of $-C(O)-$, $-S(O)_2-$, $-C(O)O-$, $-C(O)NH-$, $-C(O)NC_x^5-$, $-C(S)NH-$, $-C(S)NC_x^5-$, $-C(NH)NH-$, $-C(NH)NC_x^5-$, $-S(O)_2NH-$; and $-S(O)_2NC_x^5-$;

$R^2$ is selected from the group consisting of:
  aryl substituted with one or more groups independently selected from the group consisting of hydrogen, halo, $-C_x^6$, $-C_x^6(halo)$, $-C_x^6OH$, $-C_x^6OC_x^7$ and $-OC_x^8$; and, $C_x^8$;

$R^3$ is selected from the group consisting of aryl substituted with 1 or more substituents independently selected from the group consisting of hydrogen, halogen, hydroxy, $-C_x^9$, $-OC_x^9$, $-NH_2$, $-NHC_x^9$, $-NC_x^9C_x^{10}$, $-CO_2H$, $-CO_2C_x^9$, $-C(O)C_x^9$, $-C(O)NH_2$, $C(O)NHC_x^9$ and $C(O)NC_x^9C_x^{10}$;

$R^4$ is selected from the group consisting of $C_x^{11}$;

$R^5$, $R^6$, $R^7$ and $R^8$ are independently selected from the group consisting of hydrogen, halo, $-C_x^{12}$, $-OC_x^{12}$ and $-O(C_x^{12})O-$;

$C_x^1$, $C_x^2$, $C_x^3$, $C_x^4$, $C_x^5$, $C_x^6$, $C_x^7$, $C_x^8$, $C_x^9$, $C_x^{10}$, $C_x^{11}$, $C_x^{12}$, and $C_x^{13}$ are independent ($C_1$–$C_4$)alkyl; and, the absolute stereochemistry of centers of asymmetry are independently R or S; or, a pharmaceutically acceptable salt thereof.

2. The compound of claim 1, wherein $L^1$ is a single bond.

3. The compound of claim 1, wherein $R^1$ is a heteroalicyclic.

4. The compound of claim 3, wherein the heteroalicyclic is selected from the group consisting of:

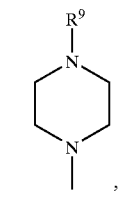

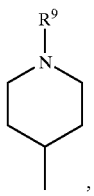

and

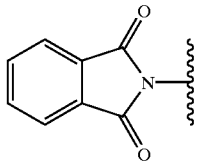

wherein $R^9$ is selected from the group consisting of hydrogen, $-C_x^2$, $-C_x^2Cl$, $-C_x^2OH$ and $-C_x^2OC(O)C_x^3$.

5. The compound of claim 4, wherein the heteroalicyclic is

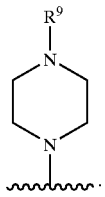

6. The compound of claim 5, wherein $R^9$ is selected from the group consisting of $CH_3-$, $-CH_2CH_2Cl$, $-CH_2CH_2OH$ and $-CH_2OC(O)CH_3$.

7. The compound of claim 5, wherein $R^9$ is $CH_3-$.

8. The compound of claim 1, wherein $R^2$ is phenyl substituted with one or more groups independently selected from the group consisting of hydrogen, halo, $-C_x^4$ and $C_x^4O-$.

9. The compound of claim 1, wherein $R^2$ is phenyl optionally substituted with one or more groups independently selected from the group consisting of fluorine, chlorine, $CH_3-$ and $CH_3O-$.

10. The compound of claim 1, wherein $L^2$ is selected from the group consisting of $-C(O)O-$, $-C(O)NH-$, $-C(O)-$ and $-S(O)_2-$.

11. The compound of claim 1, wherein $R^3$ is phenyl substituted with one or more groups independently selected from the group consisting of hydrogen, $C_x^5-$, $C_x^5O-$ and $-O(C_x^5)O-$.

12. The compound of claim 1, wherein $R^3$ is phenyl substituted with one or more groups independently selected from the group consisting of hydrogen, $CH_3-$, $CH_3O-$ and $-OCH_2O-$.

13. The compound of claim 1, wherein $R^4$ is $CH_3-$.

14. The compound of claim 1, wherein $R^5$, $R^6$, $R^7$ and $R^8$ are independently selected from the group consisting of hydrogen, halo, $-C_x^5$ and $C_x^5O-$.

15. The compound of claim 1, wherein $R^5$, $R^6$, $R^7$ and $R^8$ are independently selected from the group consisting of hydrogen, fluorine and chlorine.

16. The compound of claim 1, wherein:
L1 is a single bond; and,
R1 is

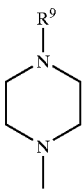

wherein $R_9$ is $CH_3$.

17. A pharmaceutical composition comprising
a pharmaceutically acceptable carrier or excipient; and,
an efflux pump inhibitor having the chemical structure:

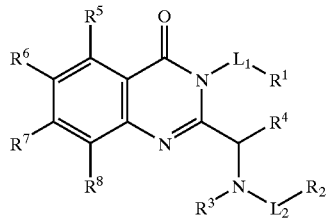

wherein:
$L^1$ is selected from the group consisting of a single bond and $C_x^1$;
$R^1$ is selected from the group consisting of:
(C$_3$–C$_7$)heteroalicyclic containing 1 nitrogen atom and 0 to 2 additional heteroatoms independently selected from the group consisting of nitrogen, oxygen and sulfur wherein the heteroalicyclic is substituted with one or more substituents independently selected from the group consisting of hydrogen, halo, hydroxy, $-C_x^2$, $=O$, $-OC_x^2$, $-C_x^2OC_x^3$, $-C_x^2OH$, $-C_x^2(halo)$, $-C_x^2OC(=O)C_x^3$, $-C_x^2NHC(=O)C_x^3$, $-C_x^2NHC(=NH)C_x^3$, $-NHC_x^2$, $-NC_x^2C_x^3$, $-C_x^2NH_2$, $-C_x^2NHC_x^3$, $-C_x^2NC_x^3C_x^4$ and $-C=C-C=C-$, wherein the end carbons of the group are covalently bonded to adjacent carbon atoms of the heteroalicyclic ring to form a carbocyclic ring, the adjacent carbon atoms of the heteroalicyclic being double-bonded to one another such that the carbocyclic ring formed is a phenyl group;
$-C_x^2NHC(=NH)C_x^3$; $-C_x^2NC_x^3C(=NH)C_x^3$ and, $-C_x^2NHC(=O)C_x^3$;
$L^2$ is selected from the group consisting of $-C(O)-$, $-S(O)_2-$, $-C(O)O-$, $-C(O)NH-$, $-C(O)NC_x^5-$, $-C(S)NH-$, $-C(S)NC_x^5-$, $-C(NH)NH-$, $-C(NH)NC_x^5-$, $-S(O)_2NH-$; and $-S(O)_2NC_x^5-$;
$R^2$ is selected from the group consisting of:
aryl substituted with one or more groups independently selected from the group consisting of hydrogen, halo, $-C_x^6$, $-C_x^6(halo)$, $-C_x^6OH$, $-C_x^6OC_x^7$ and $-OC_x^8$; and,
$C_x^8$;
$R^3$ is selected from the group consisting of aryl substituted with 1 or more substituents independently selected from the group consisting of hydrogen, halogen, hydroxy, $-C_x^9$, $-OC_x^9$, $-NH_2$, $-NHC_x^9$, $-NC_x^9C_x^{10}$, $-CO_2H$, $-CO_2C_x^9$, $-C(O)C_x^9$, $-C(O)NH_2$, $C(O)NHC_x^9$ and $C(O)NC_x^9C_x^{10}$;
$R^4$ is selected from the group consisting of $C_x^{11}$;

$R^5$, $R^6$, $R^7$ and $R^8$ are independently selected from the group consisting of hydrogen, halo, —$C_x^{12}$, —$OC_x^{12}$ and —$O(C_x^{12})O$—;

$C_x^1$, $C_x^2$, $C_x^3$, $C_x^4$, $C_x^5$, $C_x^6$, $C_x^7$, $C_x^8$, $C_x^9$, $C_x^{10}$, $C_x^{11}$, $C_x^{12}$ and $C_x^{13}$ are independently ($C_1$–$C_4$)alkyl; and, the absolute stereochemistry of centers of asymmetry are independently R or S; or, a pharmaceutically acceptable salt thereof.

18. The pharmaceutical composition of claim 17 further comprising a therapeutically effective amount of an anti-fungal agent.

19. The pharmaceutical composition of claim 18, wherein the anti-fungal agent is an azole anti-fungal agent.

20. The pharmaceutical composition of claim 19, wherein the azole anti-fungal agent is fluconazole or posaconazole.

21. A method for inhibiting the growth or proliferation of a fungal cell that employs an efflux pump resistance mechanism, comprising contacting the fungal cell with a anti-fungal agent and a fungal efflux pump inhibitor having the chemical structure:

wherein:

$L^1$ is selected from the group consisting of a single bond and $C_x^1$;

$R^1$ is selected from the group consisting of:
($C_3$–$C_7$)heteroalicyclic containing 1 nitrogen atom and 0 to 2 additional heteroatoms independently selected from the group consisting of nitrogen, oxygen and sulfur wherein the heteroalicyclic is substituted with one or more substituents independently selected from the group consisting of hydrogen, halo, hydroxy, —$C_x^2$, =O, —$OC_{x2}$, —$C_x^2OC_x^3$, —$C_x^2OH$, —$C_x^2$(halo), —$C_x^2OC(=O)C_x^3$, —$C_x^2NHC(=O)C_x^3$, —$C_x^2NHC(=NH)C_x^3$, —$NHC_x^2$; —$NC_x^2C_x^3$, —$C_x^2NH_2$, —$C_x^2NHC_x^3$, —$C_x^2NC_x^3C_x^4$ and —C=C—C=C—, wherein the end carbons of the group are covalently bonded to adjacent carbon atoms of the heteroalicyclic ring to form a carbocyclic ring, the adjacent carbon atoms of the heteroalicyclic being double-bonded to one another such that the carbocyclic ring formed is a phenyl group;
—$C_x^2NHC(=NH)C_x^3$; —$C_x^2NC_x^3C(=NH)C_x^{13}$ and, —$C_x^2NHC(=O)C_x^3$;

$L^2$ is selected from the group consisting of —C(O)—, —S(O)$_2$—, —C(O)O—, —C(O)NH—, —C(O)NC$_x^5$—, —C(S)NH—, —C(S)NC$_x^5$—, —C(NH)NH—, —C(NH)NC$_x^5$—, —S(O)$_2$NH—; and —S(O)$_2$NC$_x$—;

$R^2$ is selected from the group consisting of:
aryl substituted with one or more groups independently selected from the group consisting of hydrogen, halo, —$C_x^6$, —$C_x^6$(halo), —$C_x^6OH$, —$C_x^6OC_x^7$ and —$OC_x^8$; and,
$C_x^8$;

$R^3$ is selected from the group consisting of aryl substituted with 1 or more substituents independently selected from the group consisting of hydrogen, halogen, hydroxy, —$C_x^9$, —$OC_x^9$, —$NH_2$, —$NHC_x^9$, —$NC_x^9C_x^{10}$, —$CO_2H$, —$CO_2C_x^8$, —$C(O)C_x^9$, —$C(O)NH_2$, $C(O)NHC_x^9$ and $C(O)NC_x^9C_x^{10}$;

$R^4$ is selected from the group consisting of $C_x^{11}$;

$R^5$, $R^6$, $R^7$ and $R^8$ are independently selected from the group consisting of hydrogen, halo, —$C_x^{12}$, —$OC_x^{12}$ and —$O(C_x^{12})O$—;

$C_x^1$, $C_x^2$, $C_x^3$, $C_x^4$, $C_x^5$, $C_x^6$, $C_x^7$, $C_x^8$, $C_x^9$, $C_x^{10}$, $C_x^{11}$, $C_x^{12}$ $C_x^{13}$ are independently ($C_1$–$C_4$)alkyl; and, the absolute stereochemistry of centers of asymmetry are independently R or S; or, a pharmaceutically acceptable salt thereof.

22. The method of claim 21, wherein the anti-fungal agent is an azole anti-fungal agent.

23. The method of claim 22, wherein the azole anti-fungal agent is selected from the group consisting of fluconazole and posaconazole.

24. The method of claim 21, wherein the fungal cell is first contacted with the efflux pump inhibitor and then contacted with the anti-fungal agent.

25. The method of claim 21, wherein the fungal cell is contacted with the efflux pump inhibitor and the anti-fungal agent simultaneously.

26. The method of claim 21, wherein the fungal cell is a genus Candida cell.

27. The method of claim 26, wherein the genus Candida cell is selected from the group consisting of *C. albicans, C. krusei, C. tropicalis, C. parapsilosis* and *C. glabrata*.

28. The method of claim 21, wherein the fungal cell is a genus Aspergillus cell.

29. The method of claim 28, wherein the genus Aspergillus cell is an *Aspergillus fumigatus* cell.

30. A method for treating an infection caused by a fungus that employs an efflux pump resistance mechanism, comprising administering to a patient in need thereof a therapeutically effective amount of an anti-fungal agent and an efflux pump inhibitor having the chemical structure:

wherein:

$L^1$ is selected from the group consisting of a single bond and $C_x^1$;

$R^1$ is selected from the group consisting of:
($C_3$–$C_7$)heteroalicyclic containing 1 nitrogen atom and 0 to 2 additional heteroatoms independently selected from the group consisting of nitrogen, oxygen and sulfur wherein the heteroalicyclic is substituted with one or more substituents independently selected from the group consisting of hydrogen, halo, hydroxy, —$C_x^2$, =O, —$OC_x^2$, —$C_x^2OC_x^3$, —$C_x^2OH$, —$C_x^2$(halo), —$C_x^2OC(=O)C_x^3$, —$C_x^2NHC(=O)C_x^3$, —$C_x^2NHC(=NH)C_x^3$, —$NHC_x^2$, —$NC_x^2C_x^3$, —$C_x^2NH_2$, —$C_x^2NHC_x^3$, —$C_x^2NC_x^3C_x^4$ and —C=C—C=C—, wherein the end carbons of the group are covalently bonded to adjacent carbon atoms of the heteroalicyclic ring to form a carbocyclic ring, the adjacent carbon atoms of the heteroalicyclic being double-bonded to one another such that the carbocyclic ring formed is a phenyl group;
—$C_x^2$NHC(=NH)$C_x^3$; —$C_x^2$N$C_x^3$C(=NH)$C_x^{13}$ and, —$C_x^2$NHC(=O)$C_x^3$;

$L^2$ is selected from the group consisting of —C(O)—, —S(O)$_2$—, —C(O)O—, —C(O)NH—, —C(O)N$C_x^5$—, —C(S)NH—, —C(S)N$C_x^5$, —C(NH)NH—, —C(NH)N$C_x^5$—, —S(O)$_2$NH—; and —S(O)$_2$N$C_x^5$—;

$R^2$ is selected from the group consisting of:
aryl substituted with one or more groups independently selected from the group consisting of hydrogen, halo, —$C_x^6$, —$C_x^6$(halo), —$C_x^6$OH, —$C_x^6$O$C_x^7$ and —O$C_x^8$; and,
$C^8$;

$R^3$ is selected from the group consisting of aryl substituted with 1 or more substituents independently selected from the group consisting of hydrogen, halogen, hydroxy, —$C_x^9$—O$C_x^9$, —NH$_2$, —NH$C_x^9$, —N$C_x^9C_x^{10}$, —CO$_2$H, —CO$^2C_x^9$, —C(O)$C_x^9$, —C(O)NH$_2$, C(O)NH$C_x^9$ and C(O)N$C_x^9C_x^{10}$;

$R^4$ is selected from the group consisting of $C_x^{11}$;

$R^5$, $R^6$, $R^7$ and $R^8$ are independently selected from the group consisting of hydrogen, halo, —$C_x^{12}$, —O$C_x^{12}$ and —O($C_x^{12}$)O—;

$C_x^1, C_x^2, C_x^3, C_x^4, C_x^5, C_x^6, C_x^7, C_x^8, C_x^9, C_x^{10}, C_x^{11}, C_x^{12}$ and $C_x$ are independently ($C_1$–$C_4$)alkyl; and, the absolute stereochemistry of centers of asymmetry are independently R or S; or, a pharmaceutically acceptable salt thereof.

31. The method of claim 30, wherein the infection is caused by a genus Candida fungus.

32. The method of claim 31, wherein the genus Candida fungus is *C. albicans, C. krusei, C. tropicalis, C. parapsilosis* or *C. glabrata*.

33. The method of claim 30, wherein the infection is caused by a genus Aspergillus fungus.

34. The method of claim 33, wherein the genus Aspergillus fungus is *Aspergillus fumigatus*.

35. The method of claim 30 wherein the efflux pump inhibitor and the anti-fungal agent are administered to the organism simultaneously.

36. The method of claim 30, wherein the efflux pump inhibitor is administered to the organism followed by administration of the anti-fungal agent.

* * * * *